(12) United States Patent
Bose

(10) Patent No.: US 8,034,964 B2
(45) Date of Patent: Oct. 11, 2011

(54) PHOSPHAPLATINS AND THEIR USE IN THE TREATMENT OF CANCERS RESISTANT TO CISPLATIN AND CARBOPLATIN

(75) Inventor: Rathindra N. Bose, Athens, OH (US)

(73) Assignee: Ohio University, Athens, OH (US)

(*) Notice: Subject to any disclaimer, the term of this patent is extended or adjusted under 35 U.S.C. 154(b) by 0 days.

(21) Appl. No.: 12/722,189

(22) Filed: Mar. 11, 2010

(65) Prior Publication Data
US 2010/0233293 A1 Sep. 16, 2010

Related U.S. Application Data

(63) Continuation of application No. 12/187,376, filed on Aug. 6, 2008, now Pat. No. 7,700,649.

(60) Provisional application No. 60/954,126, filed on Aug. 6, 2007, provisional application No. 60/973,926, filed on Sep. 20, 2007.

(51) Int. Cl.
*C07F 9/09* (2006.01)
*A61K 31/28* (2006.01)
(52) U.S. Cl. ............. 556/17; 556/26; 514/492; 424/649
(58) Field of Classification Search .................. 556/17, 556/26; 514/492; 424/649
See application file for complete search history.

(56) References Cited

U.S. PATENT DOCUMENTS

| 4,234,500 | A | 11/1980 | Hoeschel |
| 4,291,027 | A | 9/1981 | Hoeschel |
| 7,342,122 | B2 | 3/2008 | Odani |

FOREIGN PATENT DOCUMENTS

| EP | 0409527 | 1/1991 |
| EP | 2177525 | 4/2010 |
| WO | 2005/000858 | 1/2005 |

OTHER PUBLICATIONS

Mishur et al., "INOR 135Platinum-(IV) phosphate complexes as potential anticancer drugs", (posted on ACS website Jul. 17, 2006).*
Bose et al., Poster, "Platinum(IV) Phosphato Complexes as Potential Anticancer Drugs", Displayed at ACS National Meeting, Sep. 10-14, 2006.*
Bose et al., Inorg. Chem., vol. 29, No. 18, pp. 3461-3467 (1990).*
Siddik ZH, "Cisplatin: mode of cytotoxic action and molecular basis of resistance, Oncongene," 22:7265-7279 (2003).

(Continued)

*Primary Examiner* — Porfirio Nazario Gonzalez
(74) *Attorney, Agent, or Firm* — Dinsmore & Shohl, LLP

(57) ABSTRACT

The present invention provides phosphaplatins, stable isolated monomeric phosphato complexes of platinum (II) and (IV), and methods of use thereof for treating cancers, including cisplatin- and carboplatin-resistant cancers. Unlike cisplatin, these complexes do not readily undergo hydrolysis and are quite soluble and stable in aqueous solutions. Moreover, these complexes—unlike cisplatin, carboplatin, and related platinum-based anti-cancer agents—do not bind DNA. Rather, data suggests that phosphaplatins trigger overexpression of fas and fas-related transcription factors and some proapoptotic genes such as Bak and Bax. Nevertheless, the complexes exhibit tremendous cytotoxicity towards cancer cells. Thus, the present invention provides novel platinum anticancer agents that have a different molecular target than those in the art.

32 Claims, 16 Drawing Sheets

I

II

III

IV

OTHER PUBLICATIONS

Slavin et al., "One- and Two-Dimensional 31P NMR Characterization of Pure Phosphato Chelates in Cytidine-5'-di- and -triphosphatoplatinum (II) complexes," J. Chem. Soc. Chem. Comm., 1256-1258 (1990).

Slavin et al., "Phosphonato Complexes of Platinum (II): Kinetics of Formation and Phosphorus-31 NMR Studies," J. Inorg. Biochem., 40, 339-347 (1990).

Sorenson CM et al., "Mechanism of cis-diamminedichloroplatinum(II)-induced cytotoxicity: role of G2 arrest and DNA double-strand breaks," Cancer Res, 48:4484-4488 (1988).

Stanko, J.A., results quoted by M. J. Cleare in "Platinum Coordination Complexes in Cancer Chemotherapy" (T. A. Connors and J. J. Roberts, Eds.), Springer-Verlag: New York, 1974; pp. 25-26.

Sulis et al., "PTEN: from pathology to biology," Trends Cell Biol, 13, 478-83 (2003).

Vaisman et al., "Cell Cycle Changes Associated With Formation of Pt-DNA Adducts in Human Ovarian Carcinoma Cells With Different Cisplatin Sensitivity," Cytometry 27:54-64 (1997).

Vleminckx et al., "Genetic manipulation of E-cadherin expression by epithelial tumour cells reveals an invasion suppressor role," Cell, 66, 107-119 (1991).

Wang et al., "Cellular Processing of Platinum Anticancer Drugs," Nature Reviews Drug Discovery, 4, 307-320 (Apr. 2005).

Wei SQ et al., "Role of ERK1/2 kinase in cisplatin-induced apoptosis in human ovarian carcinoma cells," Chin Med Sci J, 19:125-129 (2004).

Welters MJ et al., "Pharmacodynamics of cisplatin in human head and neck cancer: correlation between platinum content, DNA adduct levels and drug sensitivity in vitro and in vivo," Br J Cancer, 79:82-88 (1999).

Wernyj RP et al., "Molecular mechanisms of platinum resistance: still searching for the Achilles' heel," Drug Resist Updat, 7:227-232 (2004).

Wesseling et al., "Angiogenesis in brain tumors; pathobiological and clinical aspects," J. Neurooncol., 32:253-265 (1997).

Wood FE et al., "195Pt and 31P nuclear magnetic resonance studies of the binding of the cis-Pt(NH3)2+2 moiety to phosphate in aqueous solution," Inorganica Chimica Acta, 67:L19 (1982).

Zhang et al., "Differential sensitivity of human glioblastoma LN18 (PTEN-positive) and A172 (PTEN-negative) cells to Taxol for apoptosis," Brain Res., 1239:216-225 (2008).

International Search Report and Written Opinion in PCT/US2008/072398, mailed Mar. 5, 2009 (10 pages).

Extended European Search Report in EP08797320.2, mailed Sep. 28, 2010 (7 pages).

Abe et al., "PTEN Decreases in Vivo Vascularization of Experimental Gliomas in Spite of Proangiogenic Stimuli," Cancer Research, 63, 2300-2305 (2003).

Appleton TG et al., "Multinuclear NMR study of reactions of methylphosphonic acid, CH3PO3H2, and (aminoalkyl) phosphonic acids, NH2(CH2)nPO3H2 (n=1-3), with the cis-diamminediaquaplatinum(II) cation and cis-diamminedihydroxoplatinum(II)," Inorganic Chemistry, 25:720-725 (1986).

Belka C et al., "Why 'radiation oncology,'" Radiat Oncol, 1:1 (2006).

Beneteau, Marie et al., "Localization of Fas/CD95 into the Lipid Rafts on Down-Modulation of the Phosphatidylinositol 3-Kinase Signaling Pathway," Mol Cancer Res 2008; 6(4), 604-613 (Apr. 2008).

Birchmeier et al, "Cadherin expression in carcinomas: role in the formation of cell junctions and the prevention of invasiveness," Biochim. Biophys. Acta, 1198, 11-26 (1994).

Bose et al., Poster, "Platinum Phosphato Complexes: How They Might Work as Anticancer Agents," displayed ACS National Meeting, Mar. 25, 2007.

Bose et al., "Kinetics and Mechanisms of Platinum (II) Promoted Hydrolysis of Inorganic Polyphosphates," Inorg. Chem., 24, 3989-3996 (1985).

Bose et al., "Multinuclear NMR Studies and the Kinetics of Formation of Platinum (II)-Adenine Nucleotide Complexes," J. Am. Chem. Society, 1986, 108, 4403-4408.

Bose et al., "Phosphorus-31 NMR and Kinetic Studies of the Formation of Ortho-, Pyro- and Tri-phosphato Complexes of cis-Dichlorodiammineplatinum (II)," J. Am. Chem. Soc., 106, 3336-3343 (1984).

Bose et al., "Platinum (II) Catalyzed Hydrolysis of Pyrophosphate and Triphosphate: Phosphorus-31 NMR Characterization of Kinetic Intermediates," Inorg. Chem., 23, 1181-1183 (1984).

Calvert et al., "Early Clinical Studies with cis-Diammine-1,1-Cyclobutane Dicarboxylate Platinum II," Cancer Chemother Pharmacol 9: 140-147 (1982).

Carmeliet, P., "Angiogenesis in life, disease, and medicine," Nature 438, 932-936 (2005).

Cavallaro et al., "Cadherins and the tumour progression: is it all in a switch?," Cancer Letters, 176, 123-128 (2002).

Christian et al., Abstract #291, "Phase I and Pharmacologic Study of Ormaplatin (OP)/Tetraplatin," Proceedings of ASCO, vol. 11, Mar. 1992.

Coll M et al., "Molecular structure of the complex formed between the anticancer drug cisplatin and d(pGpG):C222(1) crystal form," J Biomol Struct Dyn, 8:315-330 (1990).

Cully et al., "Beyond PTEN mutations: the PI3K pathway as an integrator of multiple inputs during tumorigenesis," Nature Rev., 6, 184-192 (2006).

Creaven, et al., "Phase I Clinical Trial of cis-Dichloro-transdihydroxy-bis-isopropylamine platinum (IV) (CHIP)," Cancer Treat Rep 67: 795-800 (1983).

Eastman, A., "Activation of Programmed Cell Death by Anticancer Agents: Cisplatin as a Model System," Cancer Cells, vol. 2, No. 8-9, 275-280 (1990).

Eiyassaki et al., "Lipid-rafts mediate ultraviolet light-induced fas aggregation in M624 melanoma cells," Photochemistry and Photobiology, 82:787-792 (2006).

Extra et al., "Phase I study of oxaliplatin in patients with advanced cancer," Cancer Chemother Pharmacol 25: 299-303 (1990).

Folkman et al., "Angiogenesis in cancer, vascular, rheumatoid and other disease," Nat. Med., 1:27-31 (1995).

Frixen et al., "E-Cadherin-mediated Cell-Cell Adhesion Prevents Invasiveness of Human Carcinoma Cells," J. Cell. Biol., 113, 173-185 (1991).

Galanski M., "Recent developments in the field of anticancer platinum complexes," Recent Pat Anticancer Drug Discov, 1:285-295 (2006).

Giaver et al., "Chemogenomic profiling: identifying the functional interactions of small molecules in yeast," Proc Natl Acad Sci USA, 101, 793-8 (2004).

Giaver et al., "Functional profiling of the *Saccharomyces cerevisiae* genome," Nature, 418, 387-91 (2002).

Gill et al., Synthesis, Kinetics, and Mechanism of Formation of Polynuclear Hydroxo-Bridged Complexes of (trans-1,2,-Diaminocyclohexane) platinum (II), J. Am. Chem. Soc., 104, 4598-4604 (1982).

Girnun GD et al., "Regression of drug-resistant lung cancer by the combination of rosiglitazone and carboplatin," Clin Cancer Res, 14:6478-6486 (2008).

Huang H et al., "Solution structure of a cisplatin-induced DNA interstrand cross-link," Science, 270:1842-1845 (1995).

Ishida S et al., "Uptake of the anticancer drug cisplatin mediated by the copper transporter Ctrl in yeast and mammals," Proc Natl Acad Sci USA, 99:14298-14302 (2002).

Jamieson ER et al., "Structure, recognition, and processing fo cisplatin-DNA adducts," Chem Rev, 99:2467-2498 (1999).

Jemal A et al., "Cancer statitistics 2005," CA Cancer J Clin, 55:10-30 (2005).

Kelland et al., "Preclinical Antitumor Evaluation of Bis-acetatoammine-dichloro-cyclohexylamine Platinum (IV): an Orally Active Platinum Drug," Cancer Research, 53, 2581-2586 (1993).

Komatsu M et al., "Copper-transporting P-type adenosine triphosphatase (ATP7B) is associated with cisplatin resistance," Cancer Res, 60:1312-1316 (2000).

Lee et al., "Genome-wide requirements for resistance to functionally distinct DNA-damaging agents," PLoS Genetics, 235-245 (2005).

Mishur, Robert J., Dissertation: "Synthesis, Characterization, Redox Kinetics, and Assessment of DNA and Thiol Binding of a new Class of Platinum(II) and -(IV) Pyrophosphato Complexes," 197 pages (Dec. 2008).

Ohgaki et al., "Genetic pathways to primary and secondary glioblastoma," Am. J. Pathol, 170: 1445-1453 (2007).

Ohmichi M et al., "Mechanisms of platinum drug resistance," Trends Pharmacol Sci, 26:113-116 (2005).

Papetti et al., "Mechanisms of normal and tumor-derived angiogenesis," American Journal of Physiology—Cell Physiology, 282(5), C947 (2002).

Parker RJ, "Platinum-DNA adduct in head and neck cancer patients receiving cisplatin and carboplatin chemotherapy, International Journal of Oncology," 3:331 (1993).

Pasetto LM et al., "The development of platinum compounds and their possible combination," Crit Rev Oncol Hematol, 60:59-75 (2006).

Pierce et al., "Genome-wide analysis of barcoded *S. cerevisiae* gene-deletion mutants in pooled cultures," Nat Protocols (2007).

Rosenberg, B., "Platinum complex-DNA interatctions and anticancer activity," Biochemie, 1978, 60, 859-867.

Rosenberg et al., "Platinum Compounds: a New Class of Potent Antitumour Agents," Nature, vol. 222, 385-386 (1969).

Sedletska Y et al., "Cisplatin is a DNA-damaging antitumour compound triggering multifactorial biochemical responses in cancer cells: importance of apoptotic pathways," Curr Med Chem Anticancer Agents, 5:251-265 (2005).

Schellens JH et al., "Relationship between the exposure to cisplatin, DNA-adduct formation in leucocytes and tumor response in patients with solid tumors," Br J Cancer, 73:1569-1575 (1996).

Sherman et al., "Structural Aspects of Platinum Anticancer Drug Interactions with DNA," Chem. Rev., 87, 1153-1181 (1987).

Office Action in CN200880101577.4, issued May 25, 2011 (14 pages, with translation).

* cited by examiner

Figure 9
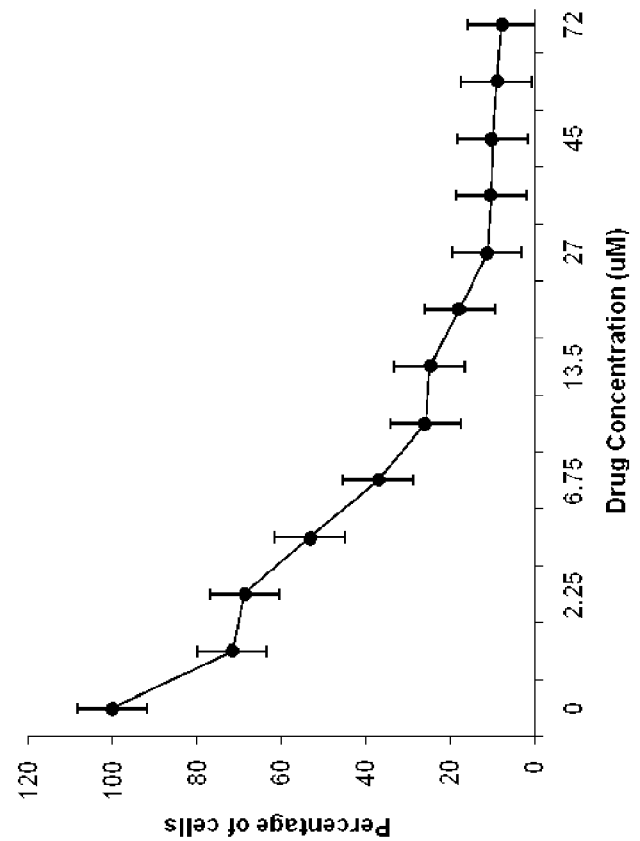
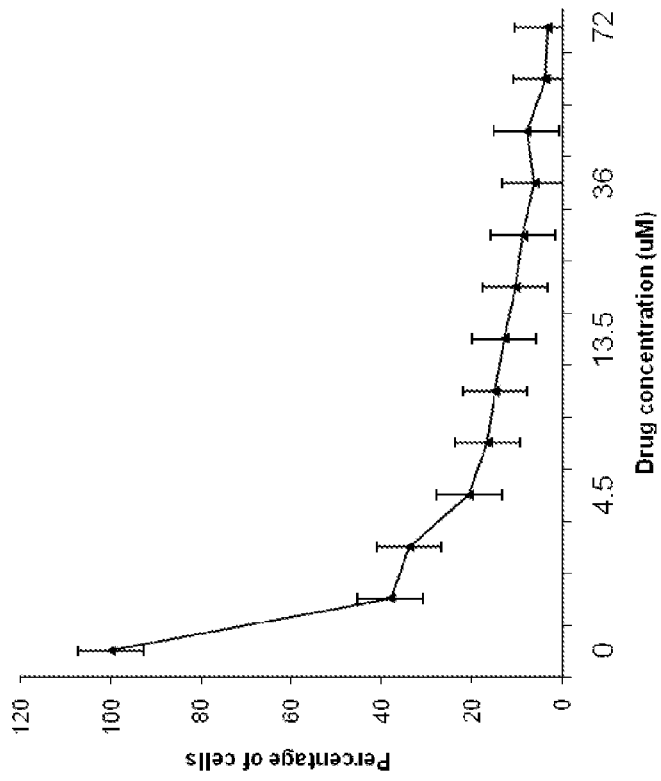

Figure 15
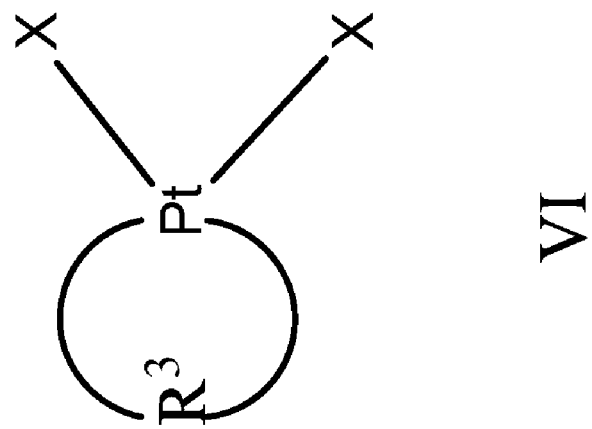
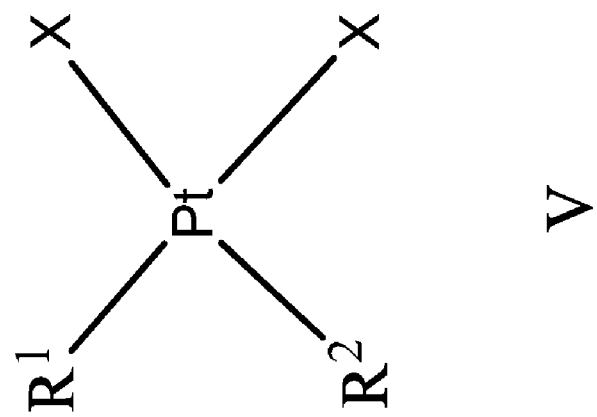

SEQUENCE LISTING

```
<160> NUMBER OF SEQ ID NOS: 1

<210> SEQ ID NO 1
<211> LENGTH: 25
<212> TYPE: DNA
<213> ORGANISM: Artificial Sequence
<220> FEATURE:
<223> OTHER INFORMATION: Completely Synthesized

<400> SEQUENCE: 1
atgatttagg tgacactata gcagt                                          25
```

US 8,034,964 B2

PHOSPHAPLATINS AND THEIR USE IN THE TREATMENT OF CANCERS RESISTANT TO CISPLATIN AND CARBOPLATIN

CROSS-REFERENCE TO RELATED APPLICATIONS

This application is a continuation of U.S. patent application Ser. No. 12/187,376, filed Aug. 6, 2008, now U.S. Pat. No. 7,700,649 which claims the benefit of priority under 35 U.S.C. Section 119(e) of U.S. Provisional Patent Application No. 60/954,126, filed Aug. 6, 2007, and U.S. Provisional Patent Application No. 60/973,926, filed Sep. 20, 2007, all of which are hereby incorporated by reference in their entirety.

BACKGROUND OF THE INVENTION

Platinum diamine complexes are well known in the art because of the tremendous success of cisdiaminedichloroplatinum(II) (cisplatin) for the treatment of ovarian, testicular, head and neck, and other forms of cancer. In addition, cisplatin is used in conjunction with other therapeutic regimens including radiation therapy. This platinum chemotherapeutic mediates apoptosis at the G2 phase of the cell cycle predominantly through transcription inhibition and through replication inhibition processes, especially at high doses. Covalent bonding to DNA through the N7 sites of guanine and adenine bases, both by intra- and inter-strand modes, is generally believed to be the key molecular event in transducing a cascade of cellular responses leading to apoptosis.

Although cisplatin is highly effective, it exhibits renal, nephro-, and neuro-toxicities. Moreover, many patients develop resistance to cisplatin treatment over time and are therefore not cured by cisplatin treatment. Two other FDA-approved platinum drugs, carboplatin (diamine-1,1-dicarcarboxylatocyclobutane-platinum(II)) and oxaliplatin (diamine-oxalatoplatinum(II)), are also believed to function in a similar manner to that of cisplatin. Carboplatin is especially effective towards cisplatin-resistant tumor cells, but relatively high doses are required to effectively treat patients who are resistant to cisplatin. Such high doses also have associated toxicities.

Many new platinum amine complexes have been synthesized and tested for their anticancer activities. However, only a few of these complexes (some of which are listed in FIG. 14) have exhibited promising results. These new complexes contain a variety of replaceable nonamine ligands, as well as nonreplaceable amine ligands that are believed to be important for DNA binding and cellular uptake. Generally, these and other relevant platinum amine complexes known in the art are synthesized by the process used for preparing cisplatin, namely where tetrachloroplatinate ($PtCl_4^{2-}$) receives amine ligands to become $PtCl_2$ (amine/diamine). Starting with the tetrochloro complex generally provides other products, and so $PtI_4^{2-}$ can also be used to ensure high yield and purity of the cis isomer, followed by conversion of $PtI_4^{2-}$ to $PtI_2$ (amine/diamine) and then into $PtCl_2$ (amine/diamine). In converting $PtI_2$ (amine/diamine) to $PtCl_2$ (amine/diamine), the di-iodo complex is converted to diaqua complex by treating the former with two equivalents of silver nitrate or other soluble silver salts at low pH. The resulting diaqua complex readily reacts with potassium chloride or hydrochloric acid to yield the dichloro complex of interest. In general, the platinum complexes of interest are synthesized from the corresponding diaqua complex at a low pH to introduce the replaceable ligands since dimerization or polymerization of the diaqua complex takes place rapidly at higher pH, yielding undesirable products.

Instead of replaceable chlorine ligands, platinum amine complexes in the art also have nitrogen, sulfur, carboxylate, and phosphonate as replaceable ligands. However, one characteristic of those complexes showing the most promise for treating cancer is a replaceable hard base ligand coordinated to platinum (a soft acid). Examples of such hard-soft combinations that have displayed excellent anticancer properties are carboxylato, carbonato, phosphonato platinum complexes.

Despite tremendous efforts to replace cisplatin with more effective chemotherapeutics, platinum (II) and platinum(IV) complexes with phosphates as the replaceable ligands have remained largely unexplored. This is primarily due to the fact that early work on platinum(II) phosphato complexes usually resulted in phosphate-bridged dinuclear complexes. Despite reports of excellent anticancer properties of some dinuclear phosphatoplatinum(II) complexes, further exploration of their applications were limited because of the poor solubility of these complexes in aqueous solutions. Although certain monomeric pyro- and triphosphate complexes are known in the art, such complexes are not suitable for pharmaceutical compositions because they undergo phosphate hydrolysis in moderately acidic solutions, resulting in insoluble dinuclear products (See U.S. Pat. No. 7,342,122 to Odani et al., describing a dimer of the monomeric complex am-2, which is described herein and in Bose et al., *Inorg. Chem.* 1985, 24, 3989-3996; see also, WO 2005/000858 to Odani et al., describing monomeric am-2 as a potential anticancer drug).

Therefore, there remains a need in the art for stable and effective alternatives to cisplatin and carboplatin for the treatment of cancers.

SUMMARY OF THE INVENTION

The present invention provides phosphaplatins, stable monomeric phosphato complexes of platinum (II) and (IV) having the general formulas shown in FIG. 1, wherein $R^1$, $R^2$, and $R^3$ each is independently selected from substituted or unsubstituted aliphatic or aromatic amines, and wherein when one of $R^1$ and $R^2$ is $NH_3$, the other of $R^1$ and $R^2$ is not $NH_3$; and wherein S is nothing or is independently selected from hydroxide, acetic acid, butyric acid, and alpha-hydroxy acids. Also provided are methods of making and isolating phosphaplatins.

The present invention further provides methods for treating cancers, including cisplatin- and/or carboplatin-resistant cancers, by administering an effective amount of phosphaplatins, either alone or in combination, with a pharmaceutically acceptable carrier, to a subject in need of such treatment.

BRIEF DESCRIPTION ON THE DRAWINGS

FIG. 1 displays structures of the platinum (II) and platinum (IV) complexes of the present invention. R1, R2, and R3 each is independently selected from substituted or unsubstituted aliphatic or aromatic amines, wherein when one of R1 and R2 is $NH_3$, the other of R1 and R2 is not $NH_3$. In certain embodiments, R1 and R2 are selected from amine, methyl amine, ethyl amine, propyl amine, isopropyl amine, butyl amine, cyclohexane amine, aniline, pyridine, and substituted pyridine. In certain embodiments, R3 is selected from ethylenediamine and cyclohexanediamine. S is independently selected from hydroxide, acetic acid, butyric acid, and alpha-hydroxy acids. In certain embodiments, pharmaceutically acceptable salts of the compounds are claimed.

FIG. 2 displays structures of some isolated complexes of the present invention, namely (A) diamine(dihydrogen pyrophosphato)platinum(II), also known as am-2; (B) cis-diamine-trans-dihydroxo(dihydrogen pyrophosphato)platinum(IV), also known as am-4; (C) 1,2-ethanediamine (dihydrogen pyrophosphato)platinum(II), also known as en-2; (D) 1,2-ethanediamine-trans-dihydroxo(dihydrogen pyrophosphato)platinum(IV), also known as en-4; (E) (trans-1,2-cyclohexanediamine)(dihydrogen pyrophosphato)platinum(II), also known as dach-2; and (F) (trans-1,2-cyclohexanediamine)-trans-dihydroxo(dihydrogen pyrophosphato) platinum (IV), also known as dach-4.

FIG. 3 displays the X-ray crystal structure of am-4 with sodium counter ion.

FIG. 4 displays the X-ray crystal structure of en-4 in its different conformations, as viewed from the pyrophosphate side.

FIG. 5 displays the extent of protonation of the complexes shown in FIG. 2, as measured by $^{31}P$ chemical shift as a function of pH. The estimated acidity constants are listed in Table 1. These data provide insight into the solubility differences of these complexes between acidic solution and neutral solution. Under the disclosed conditions at pH values below 2, these complexes are completely protonated and hence expected to exhibit reduced solubility.

FIG. 6 exhibits the differential stability of dach-2 at (A) pH 4.2 and (B) pH 8. At pH 8, no decomposition of dach-2 was observed as evidenced by the retention of the coordinated pyrophosphate ion to platinum(II) up to six days. In contrast, at pH 4.2, considerable decomposition is evident due to the appearance of the free pyrophosphate signal. Starting with the bottom spectrum in each panel, spectra were recorded at 24 hour time intervals.

FIG. 9 represents cytotoxicity of dach-2 towards (A) cisplatin-sensitive and (B) cisplatin-resistant head and neck cancer cell lines. IC50 values for dach-2 for cisplatin-sensitive cells is below 1 micromolar and for cisplatin-resistant cells, it is below 5 micromolar.

Figure 10:
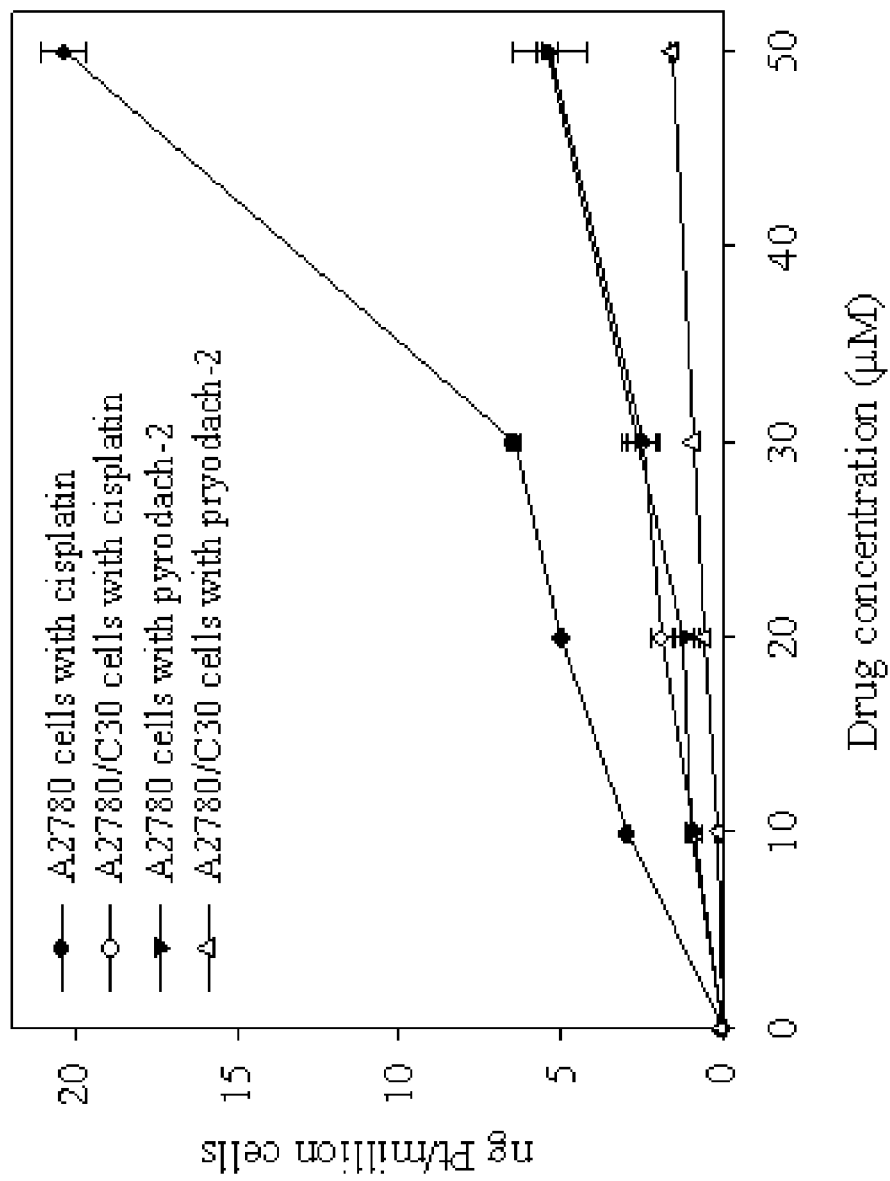

FIG. 10 shows that at a given concentration, dach-2 is taken up by cells (as determined by atomic absorption spectroscopy) in reduced quantities compared to cisplatin. For example, at 10 μM concentration, cisplatin accumulation in A2780 cells was 3.0 ng Pt/$10^6$ cells while dach-2 showed 1.0 ng Pt/$10^6$ cells. A similar trend for platinum accumulations holds for other concentrations.

Figure 11:
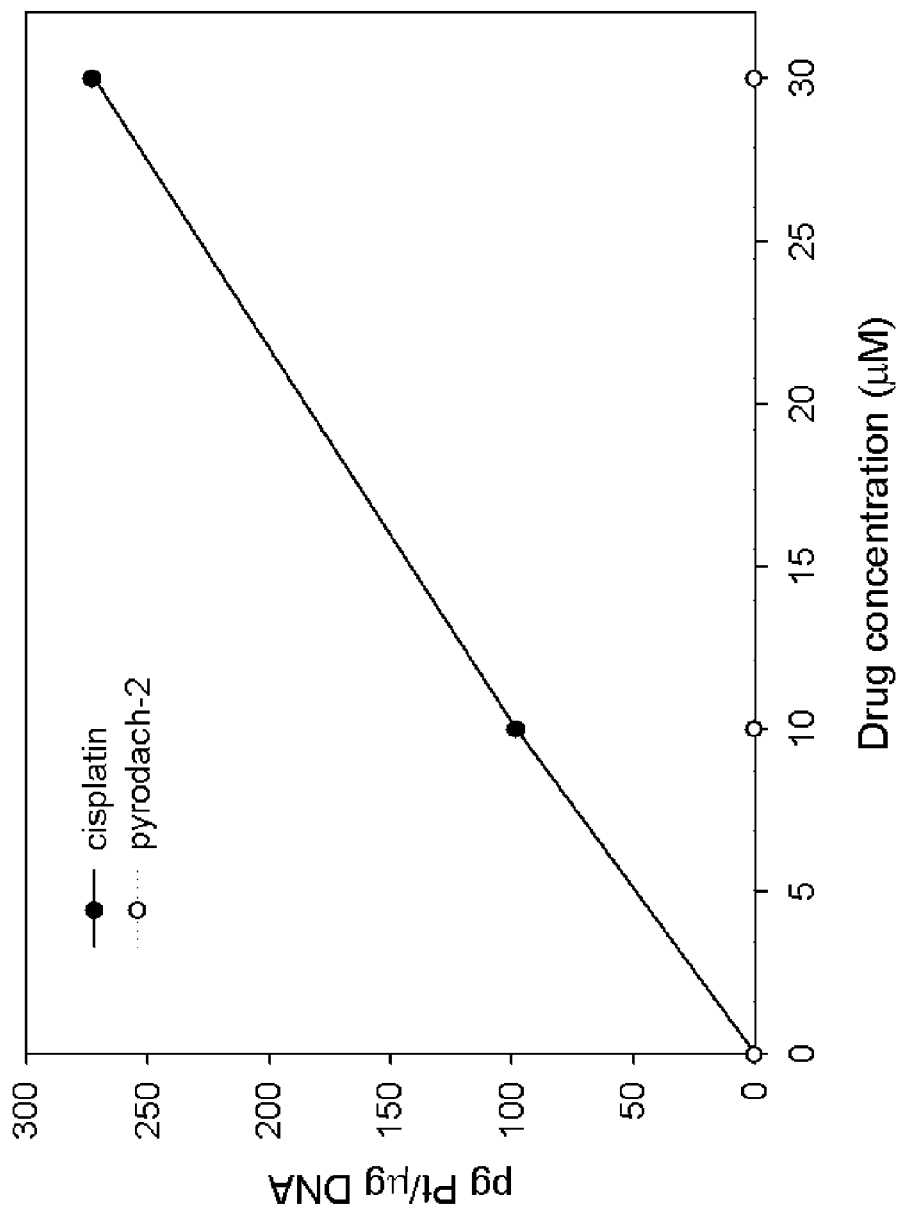

FIG. 11 shows the extent of DNA binding by cisplatin as a function of concentration in human ovarian cell line (A2780) measured by atomic absorption spectroscopy after incubating cisplatin for 2 hours. No DNA-bound platinum was detected by the same technique when A2780 cells were treated with dach-2 up to 50 micromolar concentration, even when the cells were treated for 24 hours.

Figure 12:
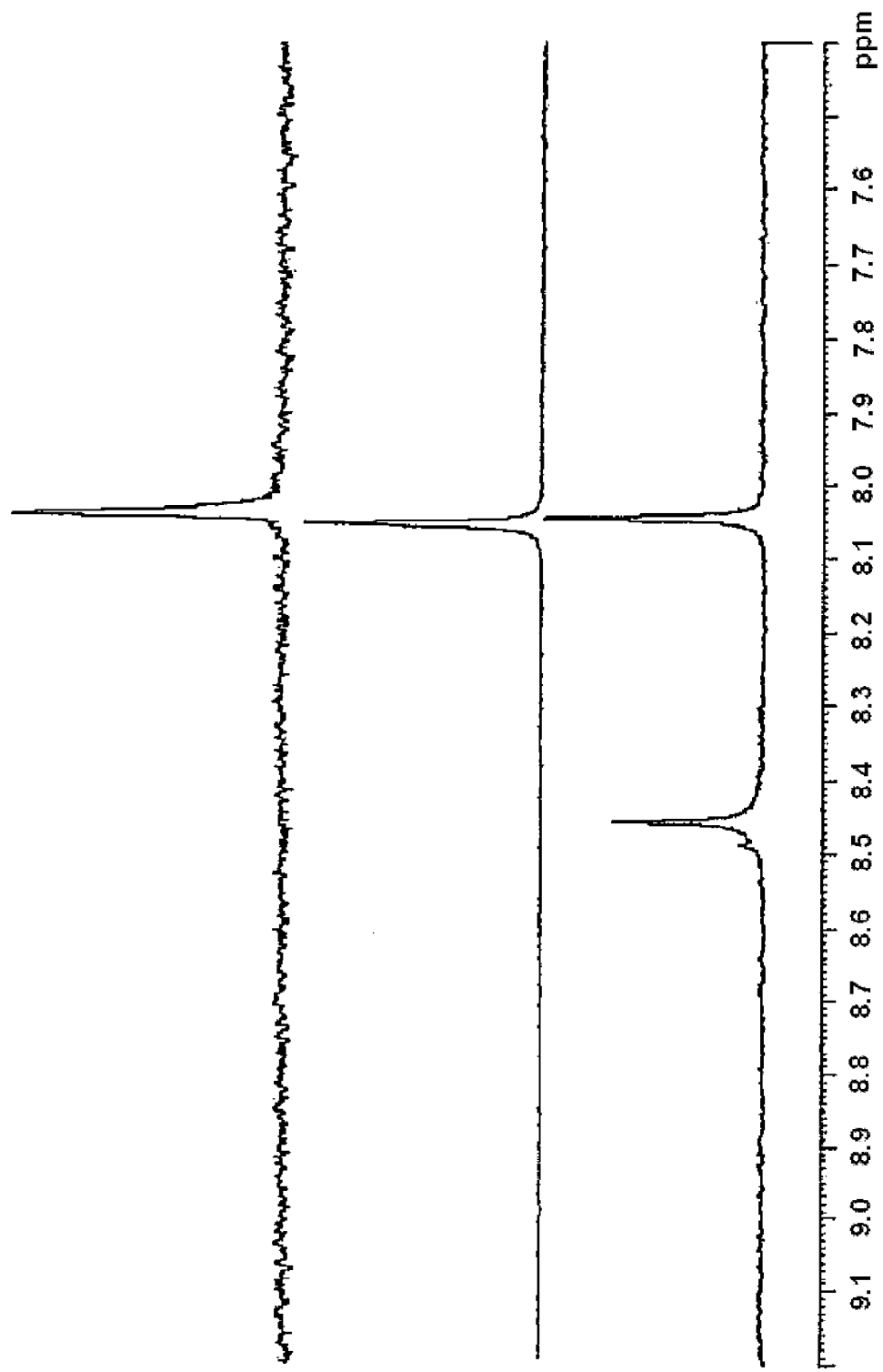

FIG. 12 is a comparison of guanine base binding (the predominant DNA binding site of cisplatin) among cisplatin (bottom), am-2 (middle), and dach-2 (top) by proton NMR spectroscopy. The top spectrum exhibits a signal for the free guanine base at 8.05 ppm for the H8 hydrogen of the purine ring, the bottom spectrum reveals an additional signal at 8.43 ppm for H8 proton due to guanine binding to cisplatin through the N7 site of the purine ring, and the middle spectrum only indicates the unbound guanine H8 signal but not platinum bound signal. The bottom spectrum was recorded after 48 hours. The middle and top spectra were recorded after 96 and 106 hours, respectively. That the complexes of the present invention do not covalently bind guanine bases (the DNA binding site for cisplatin, carboplatin, and oxaliplatin) suggests apoptotic mechanisms that are different from those proposed for cisplatin.

Figure 13:
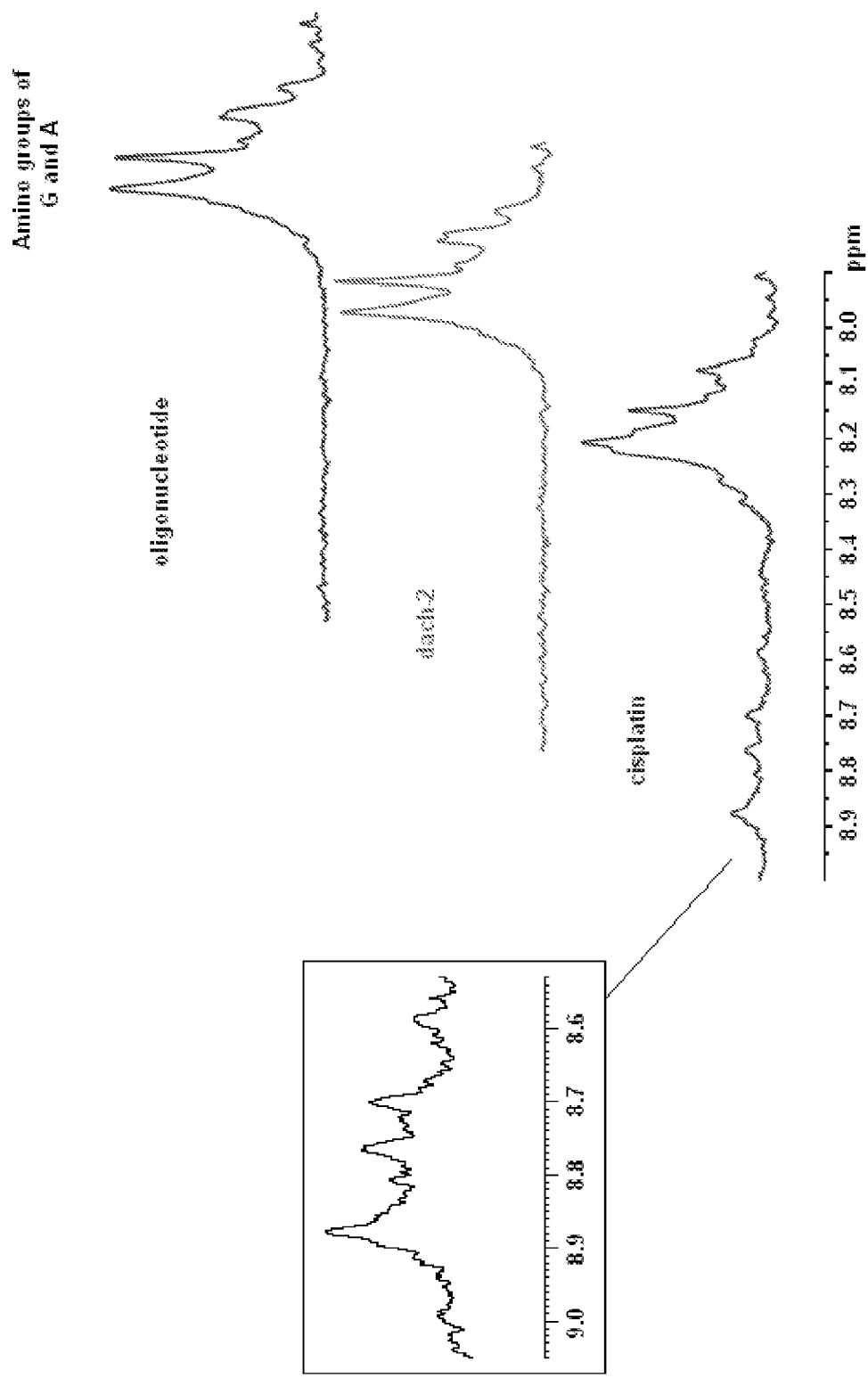

FIG. 13 shows $^1H$ NMR spectroscopy data confirming the lack of DNA binding in human ovarian cells by dach-2. In the associated experiment, dach-2 was allowed to react with double-stranded calf-thymus DNA, a synthetic oligonucleotide (5'-ATGATTTAGGTGACACTATAGCAGT-3'; SEQ ID NO:1), a dinucleotide (dGpG), and nucleotide monophosphates (5'-dGMP and 5'-dAMP) at concentrations as much as 250-times higher than those of cellular doses. The extent of DNA binding was monitored by $^1H$ NMR spectroscopy. In parallel, similar reactions with cisplatin were conducted under identical conditions. Results from a typical NMR experiment using a 25-mer oligonucleotide are displayed in the figure, which shows that dach-2 does not exhibit any measurable DNA binding, while cisplatin readily forms covalent adducts with DNA as evidenced by the formation of new signals in the region 8.4 to 8.95 ppm. However, cisplatin readily formed adducts with all the nucleotides stated above while no detectable NMR signals for dach-2 binding to nucleotides were observed even after seven days.

Figure 14:
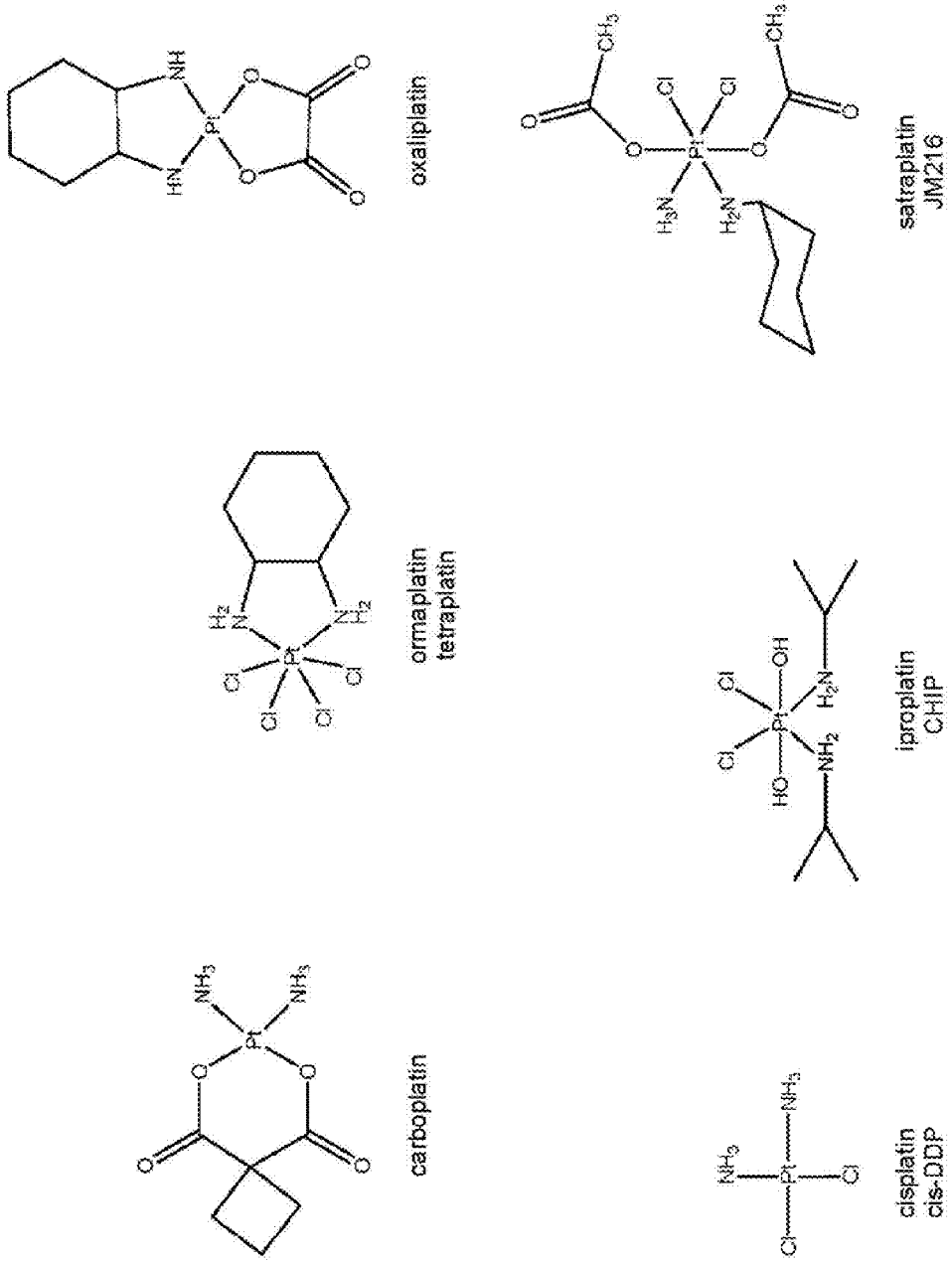

FIG. 14 displays structures of some of the active platinum complexes known in the art that are being used as drugs, are being evaluated as potential drugs, or that underwent clinical trials.

Figure 1:
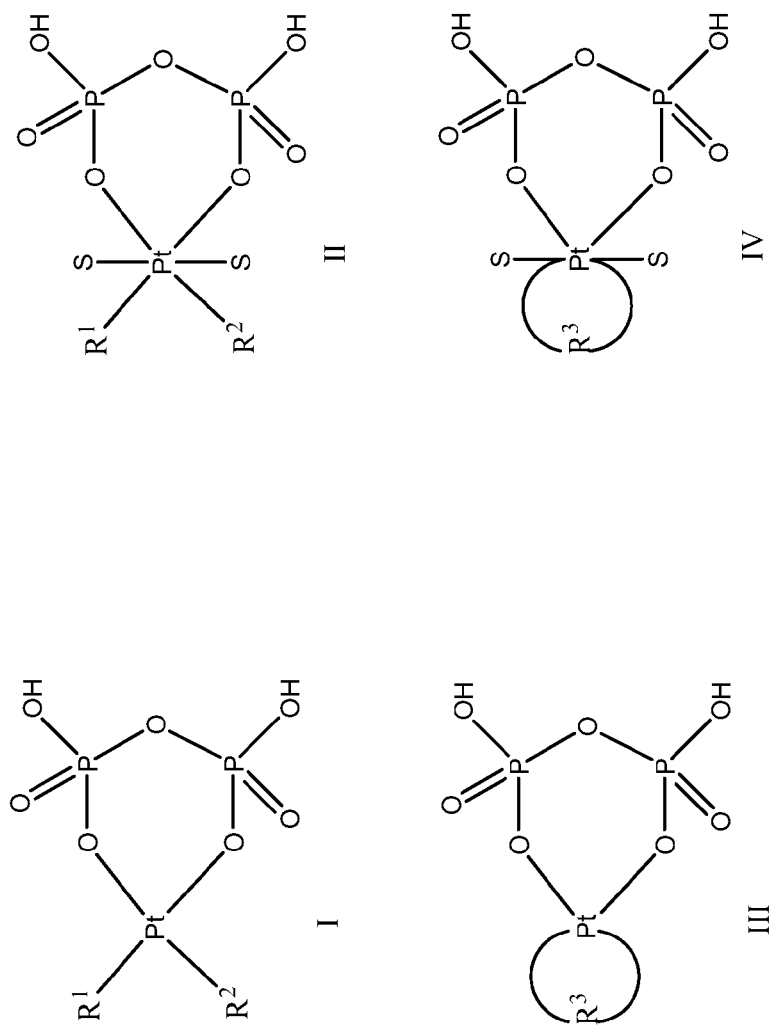

FIG. 15 displays structures of complexes used to form the phosphaplatin complexes of FIG. 1; X is halogen, R1, R2 and R3 each is independently selected from substituted or unsubstituted aliphatic or aromatic amines.

DETAILED DESCRIPTION

Provided herein are stable, monomeric platinum (II) and (IV) pyrophosphate complexes (termed phosphaplatins) for cancer treatment, including treatment of cisplatin- and/or carboplatin-resistant cancers. In general, phosphaplatins do not readily undergo hydrolysis, are soluble in aqueous solution at neutral pH, and are stable in aqueous solution at neutral pH. Furthermore, phosphaplatins show general cytotoxicity in cancer cell lines, and are effective in cell lines that are resistant to one or both cisplatin and carboplatin. Accordingly, the phosphaplatins are effective, and in some cases more effective, in inducing cancer cell death as compared to known platin cancer drugs, and exhibit desirable stability and solubility in solutions that are suitable for administration to patients. As used herein in reference to the phosphaplatins of the invention, stable refers to the resistance of the complexes to hydrolysis when maintained in aqueous solution at a pH in the range from 6-8 for a period of time from between 2 and six days.

It is believed that phosphaplatins, unlike cisplatin, carboplatin, and related platinum-based anti-cancer agents, do not covalently bind DNA. Since cisplatin resistance is believed to originate from the efficient repair of DNA damage by a variety of enzymes including nuclear excision repair enzymes, and since phosphaplatins to do not covalently bind DNA, resistance towards phosphaplatins due to the DNA repair mechanism is unlikely. Data suggests that phosphaplatins trigger overexpression of fas and fas-related transcription factors and some proapoptotic genes such as Bak and Bax. In addition, the cellular binding of phosphaplatins is much less than cisplatin, yet the phosphaplatins exhibit tremendous cytotoxicity. Thus, the present invention provides effective platinum anticancer agents that have a different molecular target than those in the art.

In some embodiments, the complexes have the general formulas shown in FIG. 1 wherein R1, R2, and R3 each is independently selected from substituted or unsubstituted aliphatic or aromatic amines, wherein when one of R1 and R2 is NH3, the other of R1 and R2 is not NH3. In certain embodiments, R1 and R2 are selected from amine, methyl amine, ethyl amine, propyl amine, isopropyl amine, butyl amine, cyclohexane amine, aniline, pyridine, and substituted pyridine. In certain embodiments, R3 is selected from ethylenediamine and cyclohexanediamine. S is independently selected from hydroxide, acetic acid, butyric acid, and alpha-hydroxy acids. In certain embodiments, pharmaceutically acceptable salts of the compounds are claimed. Thus, the anticancer agents of the present invention include, in certain embodiments, the complexes in FIG. 2.

Also provided herein are methods of synthesizing and isolating stable monomeric platinum (II) and (IV) pyrophosphate complexes. In one example, the method includes forming complexes having the formula of FIG. 1 (I) and (III) by maintaining an aqueous reaction mixture comprising excess pyrophosphate and a platinum complex of the formulas shown in FIG. 15 wherein $R^1$, $R^2$, and $R^3$ each is independently selected from substituted or unsubstituted aliphatic or aromatic amines, and wherein when one of $R^1$ and $R^2$ is $NH_3$, the other of $R^1$ and $R^2$ is not $NH_3$; and wherein X is independently selected from halogens; at a temperature of about 30 to about 60 degrees Celsius for a period of about 12 to about 18 hours at a pH from about 7 to about 9.

The complexes shown in FIG. 15 may be made in any suitable manner. In some examples as generally described in the art, cis-(amine/diamine)dichloroplatinum(II) complexes can be prepared by converting $K_2PtCl_4$ to $K_2PtI_4$ by the addition of potassium iodide. This is then reacted with the desired amine ligands. The resulting cis-(amine/diamine)diiodoplatinum(II) complexes are then transformed to the corresponding cis-(amine/diamine)diaquaplatinum(II) complexes in situ by adding two equivalents of silver nitrate. The cis-diaqua species [Pt(amine/diamine)$_2$(H$_2$O$_2$)$^{2+}$] are then converted to the cis-dichloro complexes by addition of potassium chloride.

It will be understood that other suitable reaction conditions may be used. For example, in some embodiments the temperature may be from about 35 to about 45 degrees C. Thus, the reaction temperature can be from about 30-31, 31-32, 32-33, 33-34, 34-35, 35-36, 36-37, 37-38, 38-39, 39-40, 40-41, 41-42, 42-43, 43-44, 44-45, 45-46, 46-47, 47-48, 48-49, 49-50, 50-51, 51-52, 52-53, 53-54, 54-55, 55-56, 56-57, 57-58, 58-59, 59-60 degrees C., and increments therebetween. Good results have been obtained at 40 degrees C. In some examples, the reaction is allowed to proceed from about 13 to about 16 hours. Thus the reaction time can be from about 12-13, 13-14, 14-15, 15-16, 16-17, and 17-18 hours and increments therebetween. Good results have been obtained at reaction times of 15 hours. In some examples, the pH can be from about 6-7, 7-8, and 8-9 and increments therebetween. Good results have been obtained at pH of about 8.

The method further includes subsequently concentrating the aqueous reaction mixture such that precipitates of pyrophosphate do not form. It will be understood that the aqueous reaction mixture may be concentrated in any suitable manner. For example, the aqueous reaction mixture may be concentrated by rotary evaporation.

The method further includes rapidly lowering the pH of the reaction mixture to a pH of less than about 2 by addition of a suitable acid. In some examples, nitric acid may be used to lower the pH. In some embodiments, the pH is in the range between about 1 to about 2. Good results have been obtained at pH 1

In some examples, the method also includes the reaction mixture to a temperature of between 5 degrees Celsius and ambient temperature after concentrating the reaction mixture. In other examples, the method also includes cooling the reaction mixture to a temperature of between 5 degrees Celsius and ambient temperature after lowering the pH of the reaction mixture.

In other embodiments, methods of forming complexes according to FIG. 1 (II) and (IV) are provided. The methods are as described above, but further comprise adding to the reaction mixture hydrogen peroxide, and optionally a reagent selected from the group acetate salts, butyrate salts, and salts of alpha-hydroxy acids after maintaining the reaction mixture at a temperature of about 30 to about 60 degrees Celsius for a period of about 12 to about 18 hours at a pH from about 7 to about 9.

In some examples, the optional reagent added together with hydrogen peroxide prior to concentration of the reaction mixture is selected from sodium acetate, sodium butyrate, and sodium salts of alpha-hydroxy acids. In other examples, the optional reagent added together with hydrogen peroxide prior to concentration of the reaction mixture is selected from potassium acetate, potassium butyrate, and potassium salts of alpha-hydroxy acids.

The method of synthesis and isolation of monomeric complexes described herein can be distinguished over the art since the novel method does not produce dimeric or oligomeric phosphate compounds. For example, the method reported by Bose et al. in *Inorg. Chem.* 1985, 24, 3989-3996 ("Bose 1985"), which involves isolation of Pt(NH$_3$)$_2$(H$_2$P$_2$O$_7$) (am-2) from the reaction mixture by absorbing the anionic pyrophosphate complex on an anion-exchange resin at neutral pH and eluting it with a lower pH eluant, was not useful for the synthesis and isolation of am-4, en-2, en-4, dach-2, and dach-4. When the Bose 1985 method was used, these complexes decomposed on the ion-exchange beds when separation was attempted by elution with a lower pH electrolyte. Initially, the complexes turned brownish black, followed by the formation of an insoluble black precipitate inside the ion-exchange resins. Separation of am-4, en-2, en-4, dach-2, and dach-4 from their respective reaction mixtures was possible only when the Bose 1985 method was modified as described herein. Each reaction mixture was concentrated by vacuum evaporation to the extent that unreacted pyrophosphoric acid would not precipitate out when the pH was lowered in a following step (the solubility of the pyrophosphate ligand varies greatly with pH). To initiate selective precipitation, the final concentrations were between 0.05M to 0.08M since further reduction in volume resulted in coprecipitation of the unreacted pyrophosphate that must be present in excess during the reaction. After concentrating, the reaction mixtures were cooled and the pH was rapidly lowered to 1.0 in order to induce precipitation by taking advantage of the differences in solubility between the protonated and deprotonated forms of the complexes.

Figure 5:
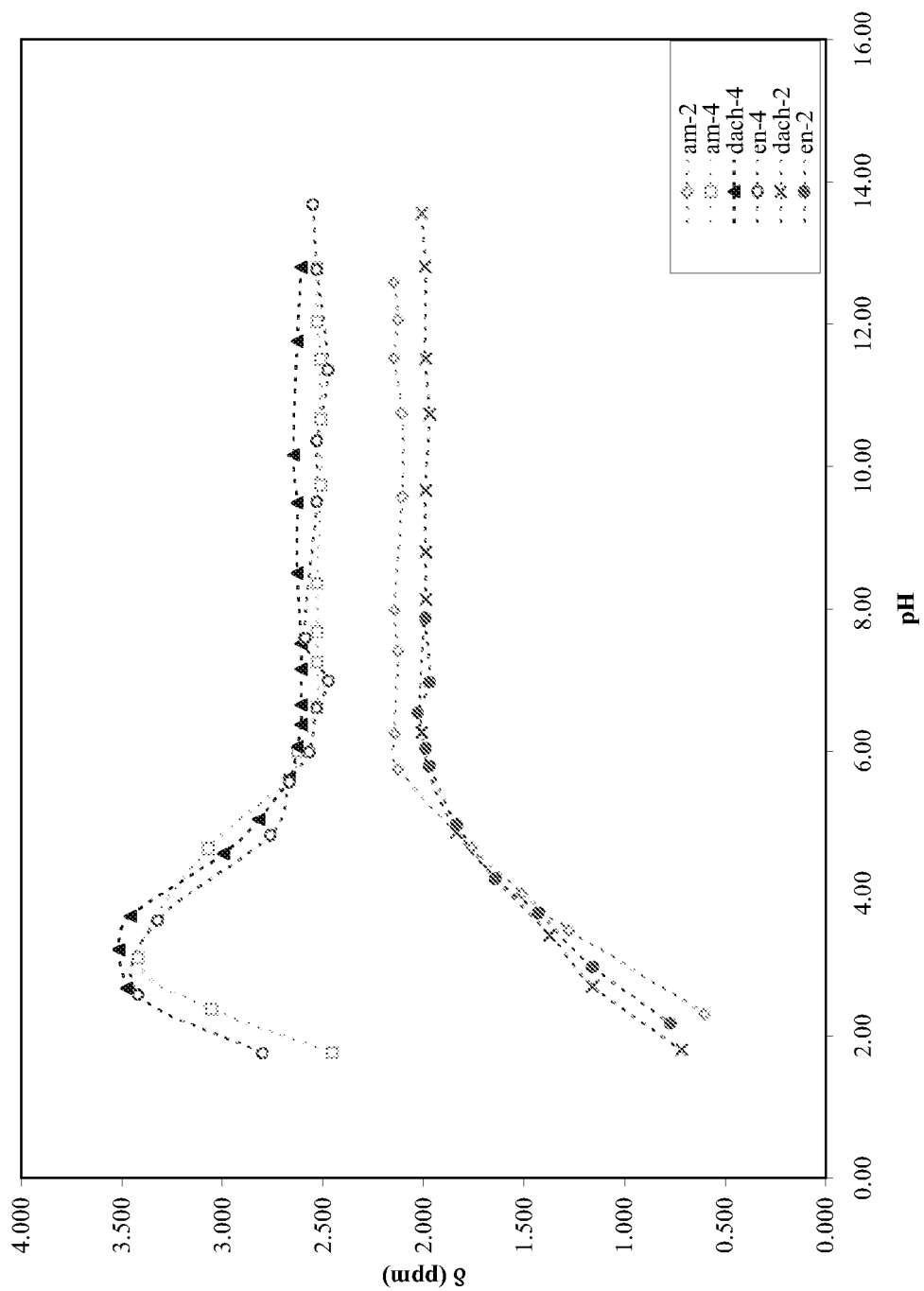
Figure 6A:
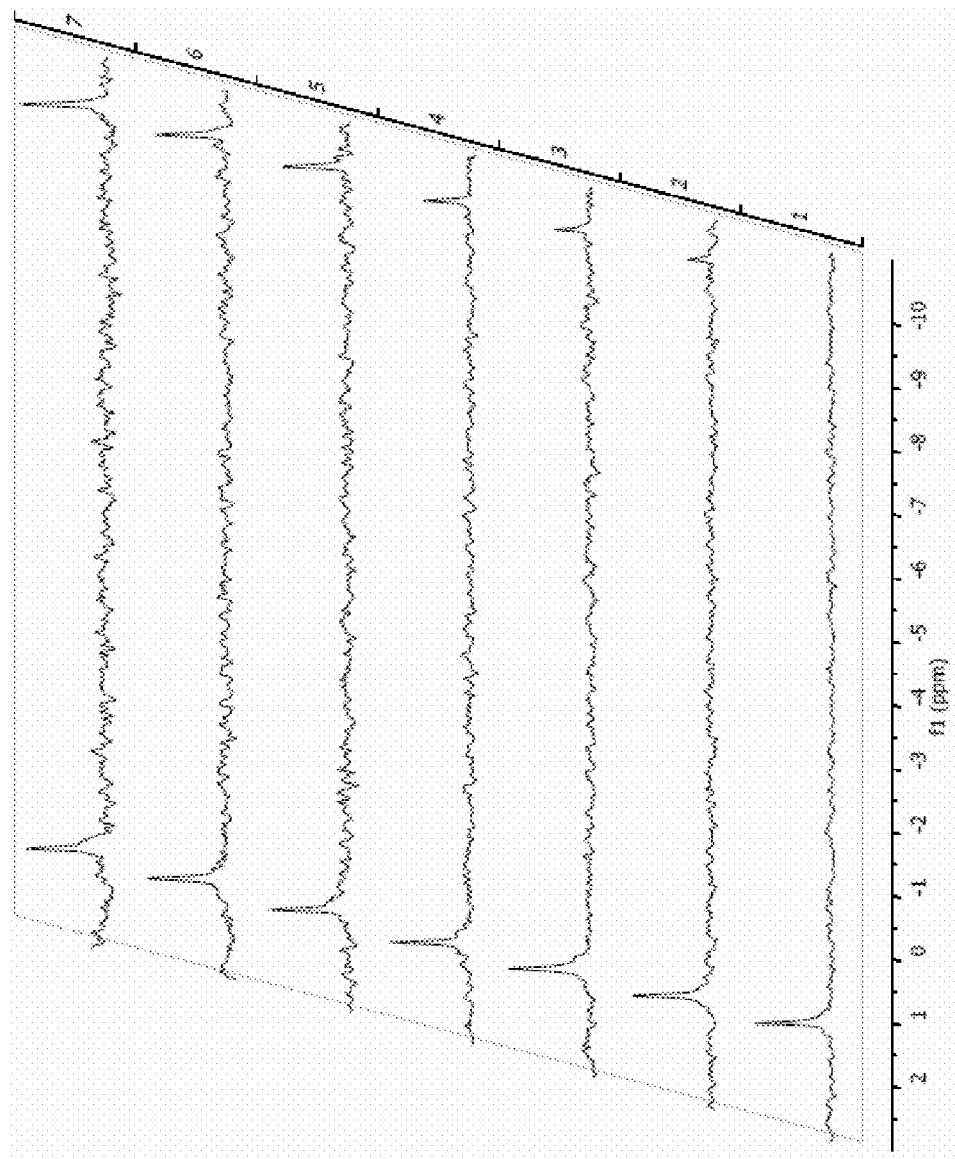
Figure 6B:
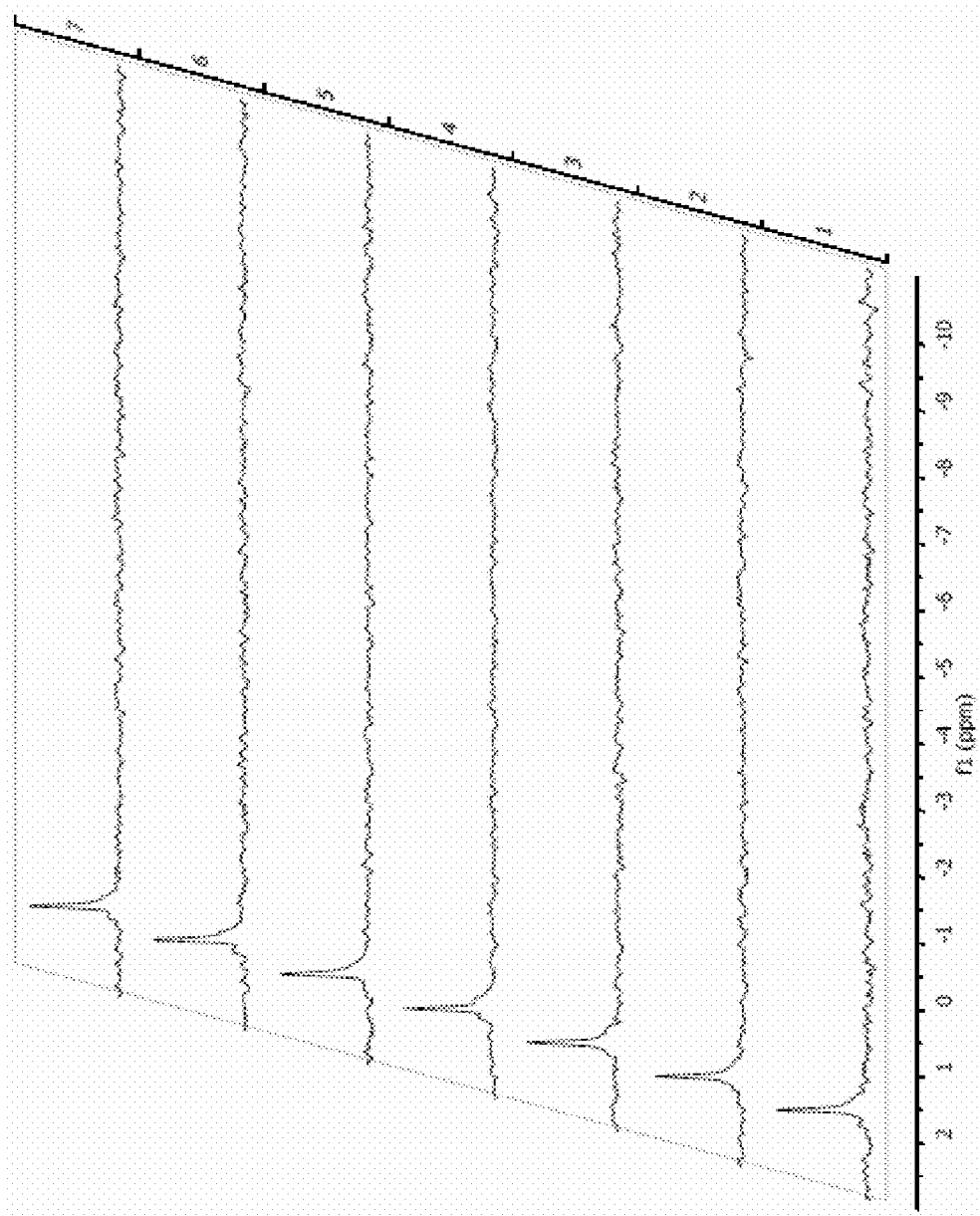
Figure 7:
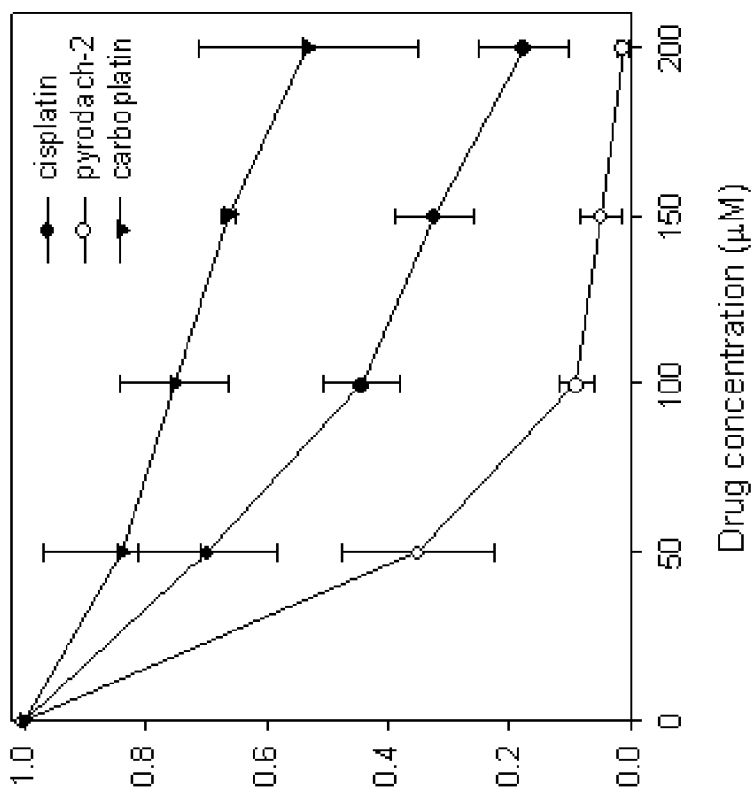
FIG. 7 is a plot of the comparison of cytotoxic effects of dach-2, cisplatin, and carboplatin as a function of micromolar concentration in cisplatin and carboplatin resistant human ovarian cell lines (A2780/C30). This cell line is resistant to 30 micromolar cisplatin and 100 micromolar carboplatin.
Figure 8:
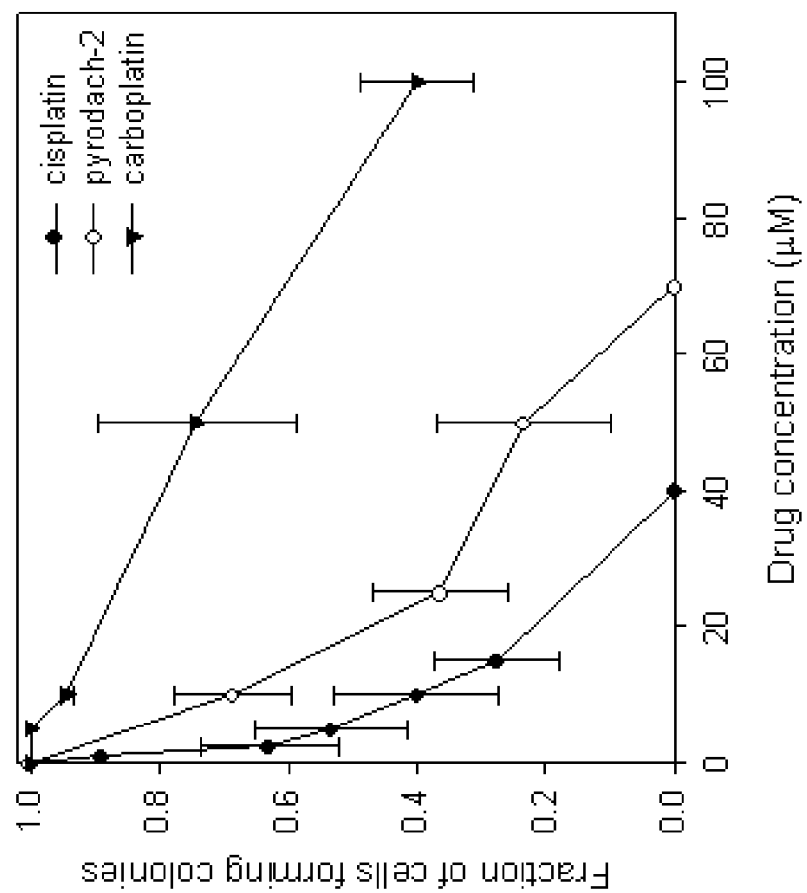
FIG. 8 is a plot comparing the cytotoxic effects of dach-2 with FDA approved cisplatin and carboplatin anticancer drugs towards human ovarian cell line (A2780).

At neutral pH, the isolated monomeric Pt(II) and Pl(IV) complexes of the present invention are stable. As indicated by $^{31}$P NMR spectra, in the range of pH 6-8 the complexes did not suffer any deligation due to the loss of either an amine or a pyrophosphate ligand over the time interval of six days at neutral pH in aqueous solution. However, in the same time interval, slow deligation due to the release of the pyrophosphate ligand was evident at pH 4.2 by the appearance of the free pyrophosphate signal at −10.3 ppm. At the same time, an insoluble pyrophosphate-bridged dinuclear platinum(II) product was formed. The data also indicates that acid decomposition is largely dependant on acidity—the higher the acidity, the faster the decomposition (See FIG. 5, Table 1, and Table 2).

TABLE 1

Chemical shifts (d, ppm) for deprotonated platinum(II) and platinum(IV) pyrophosphato-complexes and Pt—P coupling constants

| Complex | $\delta$-$^{31}$P ppm | $\delta$-$^{195}$Pt ppm | $J_{P-Pt}$ Hz |
|---|---|---|---|
| am-2 | 2.12 | −1503 | 23.44 |
| dach-2 | 1.78 | −1729 | 25.03 |
| en-2 | 1.93 | N/A | 29.73 |
| am-4 | 2.32 | 1733 | 15.38 |
| dach-4 | 2.41 | 1613 | 25.91 |
| en-4 | 2.35 | 1582 | 25.91 |

TABLE 2

Calculated pKa (-log of acidity constants) values for Pt(II)- and Pt(IV)-pyrophosphato complexes determined from phosphorus-31 chemical shifts

| Complex | pKa$_1$ | pKa$_2$ |
|---|---|---|
| am-2 | 2.9 ± 0.3 (3.8 ± 0.1) | 4.7 ± 0.2 |
| en-2 | 2.2 ± 0.1 | 4.4 ± 0.1 |
| dach-2 | 2.6 ± 0.2 (3.3 ± 0.1) | 4.4 ± 0.2 |
| am-4 | 2.0 ± 0.1 | 4.7 ± 0.1 |
| en-4 | <2 | 4.3 ± 0.1 |

The complexes of the present invention are useful for treating various cancers. Cytotoxic assays in human ovarian cell lines (A2780) and Chinese Ovarian Cells (CHO) demonstrate that these complexes are effective as a first round of treatment, and assays with both cisplatin- and carboplatin resistant Ovarian cells (C30) (See Table 3) show that these complexes are a suitable second round of treatment for resistant cancers. The complexes of the present invention are particularly desirable because they may have reduced toxicity in vivo. These complexes are taken up by cells in reduced quantities, as compared with cisplatin, indicating that lower dosage may be needed as compared to dosages for cisplatin and other platinum cancer therapeutics. For example, at 10 μM concentration, cisplatin accumulation in A2780 cells was 3.0 ng Pt/10$^6$ cells while dach-2 showed 1.0 ng Pt/10$^6$ cells, and in the resistant cell lines, dach-2 showed 1.4 ng Pt/10$^6$ cells at its IC$_{50}$ value while cisplatin showed >5 ng Pt/10$^6$ cells, yet the IC$_{50}$ value for the former complex is less than half of the latter complex (See FIG. 10 and Table 4).

TABLE 3

IC50 Values in μM concentrations for Phophaplatins, cisplatin, and carboplatin in A270 and A2780/C30, CHO cell lines

| Complex | A780 | A2780/C30 | CHO |
|---|---|---|---|
| Cisplatin | 7.5 ± 1.5 | 110 ± 11.29 | 29 ± 3 |
| Carboplatin | 90 ± 13 | >200 | >200 |
| dach-2 | 20 ± 4 | 48 ± 5 | 35 ± 5 |
| dach-4 | 180 ± 15 | 155 ± 17 | 116 ± 17 |
| am-2 | 100 ± 11 | >200 | 120 ± 30 |
| am-4 | 175 ± 22 | >200 | >200 |
| en-4 | 170 ± 33 | >200 | >200 |

TABLE 4

Comparative Cellular Accumulations (ng/10$^6$ cells) of Platinum for cisplatin and pyrodach-2 in A2780 and A2780/C30 Cell Lines

| Concentration (μM) | A2780 | | A2780/C30 | |
|---|---|---|---|---|
| | Cisplatin | dach-2 | Cisplatin | dach-2 |
| 10 | 3.00 ± 0.05 | 1.00 ± 0.10 | 1.00 ± 0.10 | 0.10 ± 0.08 |
| 20 | 5.00 ± 0.06 | 1.50 ± 0.30 | 2.00 ± 0.40 | 1.00 ± 0.02 |
| 30 | 6.00 ± 0.10 | 3.00 ± 1.00 | 2.00 ± 0.50 | 1.00 ± 0.02 |
| 50 | 20.00 ± 1.00 | 5.00 ± 0.30 | 5.00 ± 1.00 | 2.00 ± 0.10 |

The data suggests that the complexes of the present invention may induce apoptosis by different molecular and cellular mechanisms than cisplatin and other platinum drugs. First, the absence of covalent linkage (See FIG. 12 and Example 13) indicates that the complexes of the invention do not function through the DNA binding pathway. It is generally believed by those skilled in the art that acquired cisplatin resistance is due to the efficient removal of platinum from DNA by the nucleotide excision repair process. Because of the apparent absence of DNA binding, and hence the possibility that DNA repair mechanisms do not operate on the complexes of the invention, cellular resistance to the complexes may be eliminated. This conclusion finds support from the cytotoxicity data showing that dach-2 is active in both cisplatin and carboplatin resistant cell lines (See Table 3).

Second, evidence that the complexes of the present invention induce apoptosis by different molecular and cellular mechanisms than cisplatin and other platinum drugs comes from experiments where dach-2 was allowed to react with cysteine and glutathione (data not shown). The pyrophosphate ligand of dach-2 was readily replaced with concomitant ligation through the thiol, indicating possible protein anchoring sites of the cellular surface proteins through cysteine or methionine residues.

Third, evidence that the complexes of the present invention induce apoptosis by different molecular and cellular mechanisms than cisplatin and other platinum drugs also comes from experiments involving the over-expression of fas and its associated members (See Example 11). Such over-expression in response to the complexes of the invention implies that signal transduction pathways other than DNA-damaging pathways are most likely involved in exhibiting the cytotoxic activities of the complexes of the invention. On average, fas was over-expressed by a factor of six when cells were treated with complexes of the present invention, while no significant over-expression was observed in cells treated with cisplatin.

As described herein, the complexes of the present invention are as effective or more effective than commonly used cisplatin and carboplatin, thus providing a method of cancer treatment for patients who previously lacked effective alternatives to cisplatin and carboplatin treatment. However, a patient need not have previously been treated with cisplatin or carboplatin in order to be treated with the complexes and methods described herein. Administration of the treatment can be performed in a hospital or other medical facility by medical personnel.

The complexes of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including, but not limited to, improved survival rate or more rapid recovery, or improvement or elimination of symptoms and other indicators as are selected as appropriate measures by those skilled in the art. The complexes of the present invention can be administered to animals, including mammals.

In the method of treatment of the present invention, the complexes of the present invention can be administered in various ways. It should be noted that they can be administered as the complex and can be administered alone in aqueous solution taking advantage of the excellent solubility of these complexes, or as an active ingredient in combination with pharmaceutically acceptable carriers, diluents, adjuvants and vehicles. The complexes can be administered orally, subcutaneously or parenterally including intravenous, intraarterial, intramuscular, intraperitoneally, intratonsillar, and intranasal administration as well as intrathecal and infusion techniques. Implants of the complexes are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the complexes of the present invention parenterally, they will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for the compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the complexes.

Sterile injectable solutions can be prepared by incorporating the complexes utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the complexes utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Many other such implants, delivery systems, and modules are well known to those skilled in the art.

The invention is further described in detail by reference to the following experimental examples. These examples are provided for the purpose of illustration only, and are not intended to be limiting. Thus, the invention should be construed to encompass any and all variations which become evident as a result of the teaching provided herein.

The above description and the examples that follow demonstrate synthesis of pyrophosphato platinum complexes in a manner different from previously disclosed methods of synthesis. These complexes have been shown to have anticancer activities, including in cisplatin- and carboplatin-resistant cancers. Unexpectedly, the anticancer activities shown are comparable to and active at relatively lower doses than some currently administered platinum complexes. Also unexpectedly, data suggests that the complexes of the present invention have a different mechanism of action than currently administered platinum complexes, namely that they do not bind DNA during treatment. Thus, the complexes of the present invention represent a novel class of platinum therapeutics useful for treating cancers, including cisplatin- and carboplatin-resistant cancers where effective treatment has previously been hard to obtain.

The invention is described herein in an illustrative manner, and it is to be understood that the terminology used is intended to be in the nature of words of description rather than of limitation. Obviously, many modifications and variations of the present invention are possible in light of the teachings herein. It is, therefore, to be understood that within the scope of the appended claims, the invention may be practiced otherwise than as specifically described.

Example 1

Diamine(dihydrogen pyrophosphato)platinum(II) (am-2)

Sodium pyrophosphate decahydrate (0.4 g) and 0.1 g of cisplatin were dissolved in 250 mL of distilled water, pH 8, and incubated at 40 degrees C. for 15 hours. Following the incubation period, the solution was concentrated to 5-10 mL by rotary evaporation and filtered to remove any unreacted starting material. Rapidly lowering the pH to approximately 1.0 by addition of 1 N $HNO_3$ precipitated the product as a light yellow powder. Precipitation was completed by cooling on ice, and the product was isolated by vacuum filtration and washed with cold water and acetone. Yield $Pt(NH_3)_2$ $(H_2P_2O_7)$: 0.04 g (30%). The $^{31}P$ NMR spectrum displays a single peak at 2.12 ppm, pH 7.99 with respect to 85% phosphoric acid as an external reference. $^{195}$Pt NMR resonance is detected at −1503 ppm.

Example 2

Cis-diamine-trans-dihydroxo(dihydrogen pyrophosphato)platinum (IV) (am-4)

Sodium pyrophosphate decahydrate (0.4 g) and 0.1 g of cisplatin were dissolved in 250 mL of distilled water, pH 8, and incubated at 40 degrees C. for 15 hours. Following the incubation period, 1 mL 30% $H_2O_2$ was added to the reaction mixture, and it was allowed to react for a further 3 hours. The solution was then concentrated to 5-10 mL by rotary evaporation and filtered to remove any unreacted starting material. Rapidly lowering the pH to approximately 1.0 by addition of 1 N $HNO_3$ precipitated the product as a light yellow powder. Precipitation was completed by cooling on ice, and the product was isolated by vacuum filtration and washed with cold water and acetone. Yield cis, trans-Pt(NH$_3$)$_2$(OH)$_2$(H$_2$P$_2$O$_7$): 0.05 g (34%). The $^{31}$P NMR spectrum displays a single peak at 2.32 ppm, pH 8.11, with a $^{195}$Pt—$^{31}$P coupling constant of 15.4 Hz. The $^{195}$Pt NMR spectrum shows a pentet at 1733 ppm with a $^{195}$Pt—$^{14}$N coupling constant of 232 Hz.

Example 3

1,2-Ethanediamine(dihydrogen pyrophosphato)platinum(II) (en-2)

Sodium pyrophosphate decahydrate (0.4 g) and 0.1 g of dichloro(ethylenediamine)platinum(II) were dissolved in 250 mL of distilled water, pH 8, and incubated at 40 degrees C. for 15 hours. Following the incubation period, the solution was concentrated to 5-10 mL by rotary evaporation and filtered to remove any unreacted starting material. Rapidly lowering the pH to approximately 1.0 by addition of 1 N $HNO_3$ did not precipitate the product. The product was characterized in situ by $^{31}$P NMR. A single peak is observed at 1.93 ppm in the $^{31}$P NMR spectrum with a $^{195}$Pt—$^{31}$P constant of 29.73 Hz.

Example 4

1,2-Ethanediamine-trans-dihydroxo(dihydrogen pyrophosphato)platinum(IV) (en-4)

Sodium pyrophosphate decahydrate (0.4 g) and 0.1 g of dichloro(ethylenediamine)platinum(II) were dissolved in 250 mL of distilled water, pH 8, and incubated at 40 degrees C. for 15 hours. Following the incubation period, 1 mL 30% $H_2O_2$ was added to the reaction mixture, and it was allowed to react for a further 3 hours. The solution was then concentrated to 5-10 mL by rotary evaporation and filtered to remove any unreacted starting material. Rapidly lowering the pH to approximately 1.0 by addition of 1 N $HNO_3$ precipitated the product as a light yellow powder. Precipitation was completed by cooling on ice, and the product was isolated by vacuum filtration and washed with cold water and acetone. Yield trans-Pt(OH$_2$)(C$_2$H$_8$N$_2$)(H$_2$P$_2$O$_7$): 0.07 g (49%). The $^{31}$P NMR spectrum displays a single peak at 2.30 ppm, pH 8.13, with a $^{195}$Pt—$^{31}$P coupling constant of 25.9 Hz. The $^{195}$Pt NMR spectrum showed a broad peak at 1582 ppm.

Example 5

(Trans-1,2-cyclohexanediamine)(dihydrogen pyrophosphato)platinum(II) (dach-2)

Sodium pyrophosphate decahydrate (0.4 g) and 0.1 g of dichloro(trans-1,2-diaminocyclohexyl)platinum(II) were dissolved in 250 mL of distilled water, pH 8, and incubated at 40 degrees C. for 15 hours. Following the incubation period, the solution was concentrated to 5-10 mL by rotary evaporation and filtered to remove any unreacted starting material. Rapidly lowering the pH to approximately 1.0 by addition of 1 N $HNO_3$ precipitated the product as a light yellow powder. Precipitation was completed by cooling on ice, and the product was isolated by vacuum filtration and washed with cold water and acetone. Yield trans-Pt(C$_6$H$_{14}$N$_2$)(H$_2$P$_2$O$_7$): 0.05 g (38%). The $^{31}$P NMR spectrum displays a single peak at 1.78 ppm, pH 7.93 with a $^{195}$Pt—$^{31}$P constant of 25.03 Hz. $^{195}$Pt NMR signal is recorded at −1729 ppm.

Example 6

(Trans-1,2-cyclohexanediamine)-trans-dihyroxo(dihydrogen pyrophosphato)platinum(IV) (dach-4)

Sodium pyrophosphate decahydrate (0.4 g) and 0.1 g of dichloro(trans-1,2-diaminocyclohexyl)platinum(II) were dissolved in 250 mL of distilled water, pH 8, and incubated at 40 degrees C. for 15 hours. Following the incubation period, 1 mL 30% $H_2O_2$ was added to the reaction mixture, and it was allowed to react for a further 3 hours. The solution was then concentrated to 5-10 mL by rotary evaporation and filtered to remove any unreacted starting material. Rapidly lowering the pH to approximately 1.0 by addition of 1 N $HNO_3$ precipitated the product as a light yellow powder. Precipitation was completed by cooling on ice, and the product was isolated by vacuum filtration and washed with cold water and acetone. Yield trans-Pt(OH$_2$)(C$_6$H$_{14}$N$_2$)(H$_2$P$_2$O$_7$): 0.07 g (52%). The $^{31}$P NMR spectrum displays a single peak at 2.41 ppm, pH 7.95, with a $^{195}$Pt—$^{31}$P coupling constant of 25.9 Hz. The $^{195}$Pt NMR spectrum showed a broad peak at 1613 ppm.

Example 7

Figure 2:
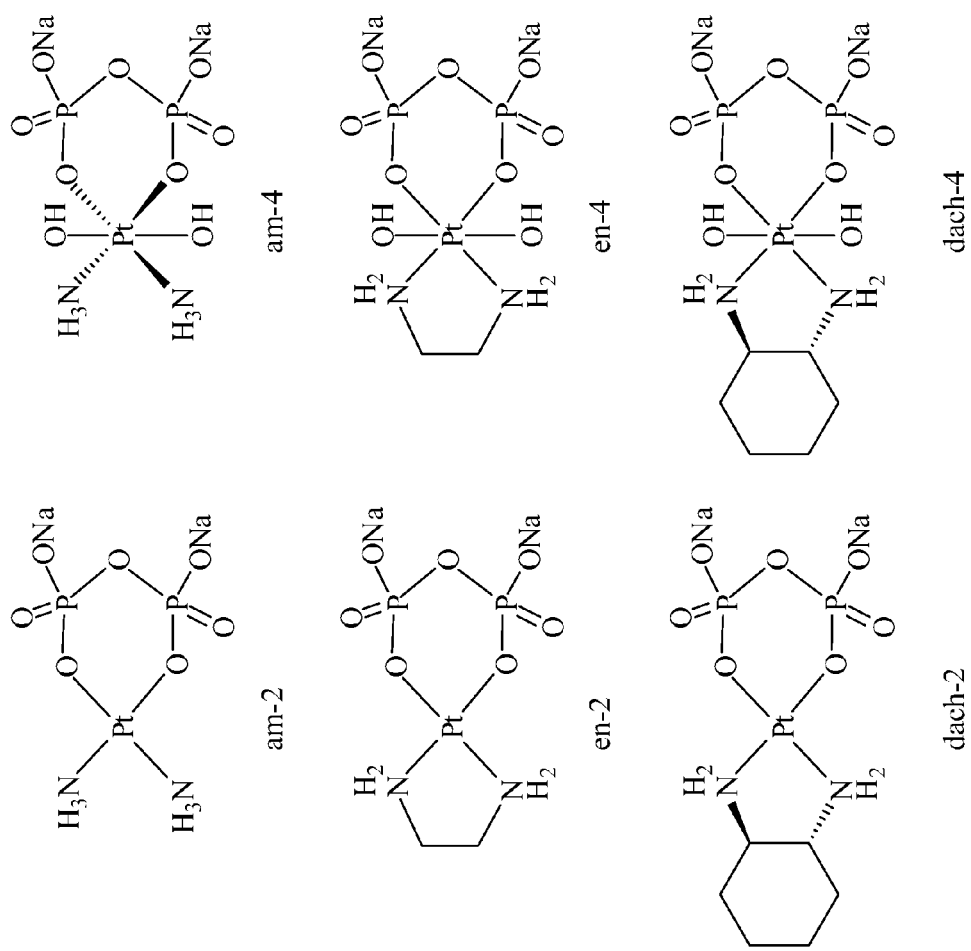
Figure 3:
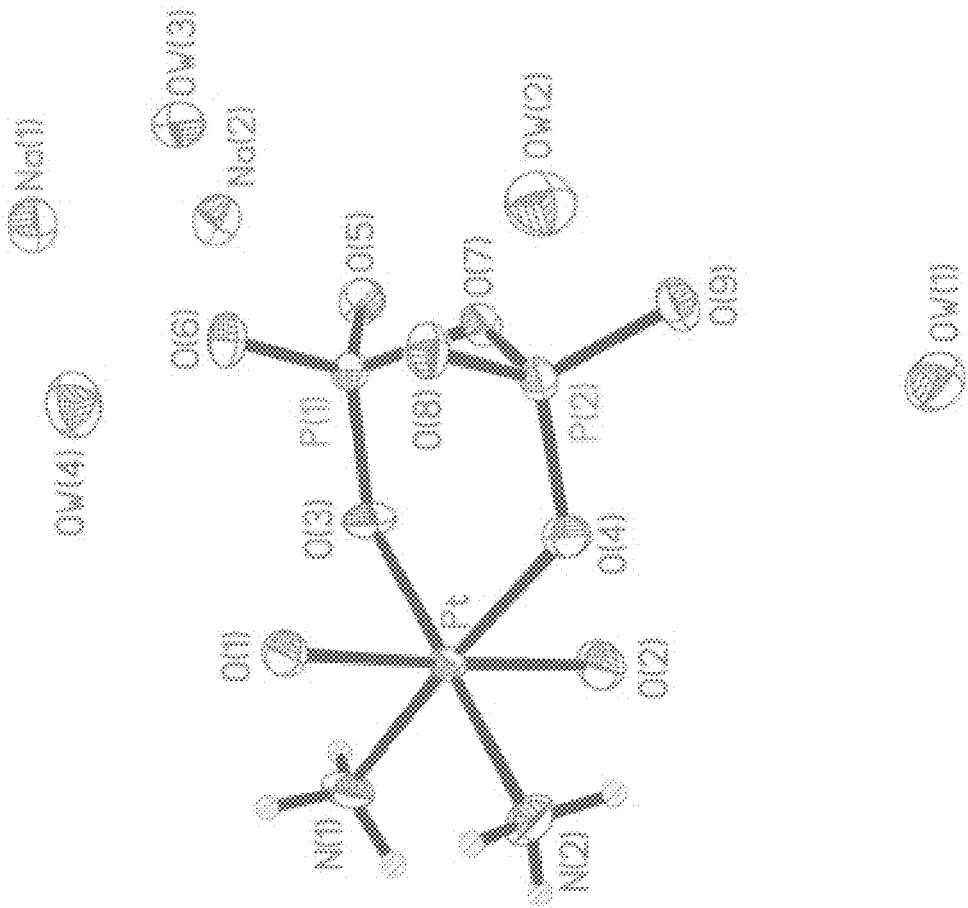
Figure 4:
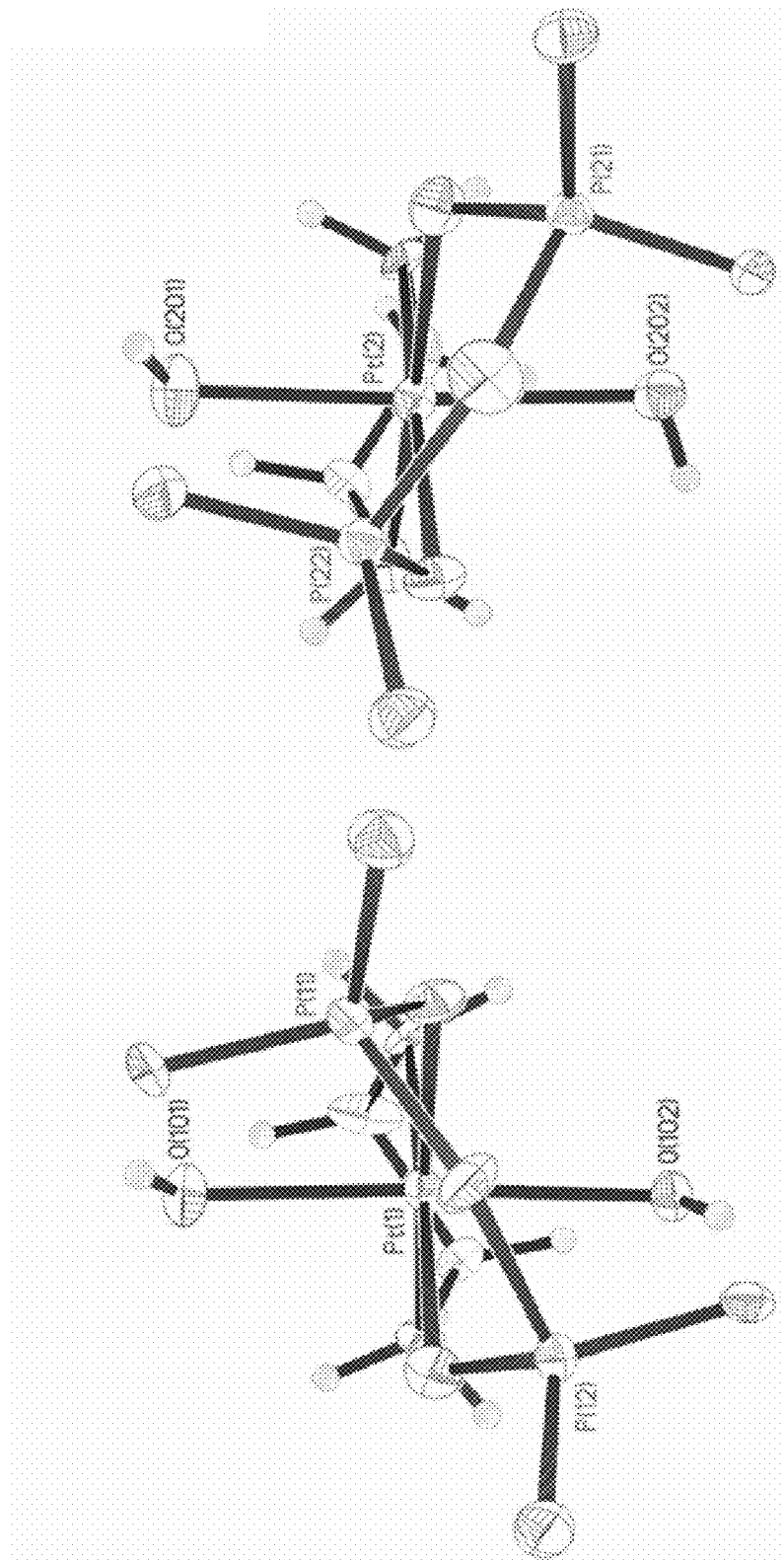

$^{31}$P NMR spectroscopy can be used to confirm that the respective diamine(pyrophosphato)platinum(II) and diamine(dihydroxo)(pymphosphalo) platinum (IV) complexes shown in FIG. 2 and described in Examples 1-6 were synthesized and isolated by the novel method described herein.

Each of the complexes exhibited a single $^{31}$P NMR resonance with chemical shifts in the range 1.78-2.12 ppm. These chemical shifts are 9-11 ppm downfield compared to the free pyrophosphate ligand, consistent with the observed coordination chemical shifts for phosphate chelates reported in the art. Monodentate pyrophosphato complexes were not detected in the final products, as revealed by the absence of the expected two sets of doublets. The $^{31}$P NMR data also showed that the oxidation of Pt(II) complexes to Pt(IV) complexes by $H_2O_2$ was selective, as evidenced by the formation of a single pyrophosphatoplatinum(IV) complex in each case.

Example 8

Human ovarian cancer cells, A2780, were obtained from Dr. Thomas Hamilton (Fox Chase Cancer Center, Philadelphia, Pa.). Cells were cultured on monolayer using RPMI 1640 supplemented with 10% fetal bovine serum, 2 mM glutamine, 0.25 units/mL insulin and penicillin/streptomycin in a 37 degrees C. incubator continuously gassed with 5% $CO_2$. Cells were subcultured using 0.0625% trypsin in HBSS to maintain cells in exponential growth.

IC50 values were determined using a clonogenic assay. Briefly, 500 A2780 cells from a single cell suspension were plated onto 60 mm Petri plates 24 hours before drug treatment to permit cell attachment. On the day of drug treatment, the medium was decanted and replaced with the drug and these treated cells were placed back into the 37 degrees C. incubator for 1 hour. Triplicate plates were set up for each drug concentration. After the 1 hour drug treatment, the drug containing medium was decanted and replaced with fresh medium. These plates were returned to the 37 degrees C. incubator for 1 week for colony formation. Colonies were fixed and stained using 2% crystal violet in absolute methanol. Colonies containing more than 50 cells were scored. The number of scored colonies from the triplicate plates was averaged and this number was divided by the number of cells plated to obtain a value for the fraction of cells forming colonies. These values for fraction of cells forming colonies were then corrected for plating efficiency by dividing it by the number of cells forming colonies in plates that were not treated with drug.

Table 3 shows the anticancer activity of the complexes described herein, expressed as IC50 values, as compared to cisplatin and carboplatin. As can be seen from the data, dach-2 exhibits better performance than both cisplatin and carboplatin in resistant cell lines. Furthermore, dach-4 shows much superior activity to carboplatin. Data also shows that dach-4 is equally or more effective towards cisplatin/carboplatin resistant cancer cells and cisplatin sensitive cells, further indicating that phosphaplatins may not develop resistance.

Unlike cisplatin and carboplatin, the phosphato complexes of the present invention are predicted to exhibit less toxicity due to the presence of phosphato ligands which might help efficiently transport these complexes to the cell. Furthermore, unlike cisplatin, these phosphato complexes did not exhibit any measurable binding to DNA within 72 hours, as shown in FIG. 12. Cisplatin is believed to function by binding genomic DNA. Thus, the phosphato complexes of the present invention have different cellular targets.

Example 9

A cisplatin-resistant Ovarian cell line (C30) (Hamaguchi, et al., 1993), obtained from Dr. Thomas Hamilton (Fox Chase Cancer Center, Philadelphia, Pa.), was treated with the monomeric platinum complexes of the present invention (shown in FIG. 2). This cell line is also cross resistant to carboplatin. Cells were cultured on monolayer using RPMI 1640 supplemented with 10% fetal bovine serum, 2 mM glutamine, 0.25 units/mL insulin and penicillin/streptomycin in a 37 degrees C. incubator continuously gassed with 5% $CO_2$. Cells were subcultured using 0.025% trypsin in HBSS to maintain cells in exponential growth.

IC50 values were determined using a clonogenic assay. Briefly, 500 C30 cells from a single cell suspension were plated onto 60 mm Petri plates 24 hours before drug treatment to permit cell attachment. On the day of drug treatment, the medium was decanted and replaced with the drug and these treated cells were placed back into the 37 degrees C. incubator for 1 hour. Triplicate plates were set up for each drug concentration. After the one hour drug treatment, the drug containing medium was decanted and replaced with fresh medium. These plates were returned to the 37 degrees C. incubator for 1 week for colony formation. Colonies were fixed and stained using 2% crystal violet in absolute methanol. Colonies containing more than 50 cells were scored. The number of scored colonies from the triplicate plates was averaged and this number was divided by the number of cells plated to obtain a value for the fraction of cells forming colonies. These values for fraction of cells forming colonies were then corrected for plating efficiency by dividing them by the number of cells forming colonies in plates that were not treated with drug.

Example 10

The UMSCC10b (Cisplatin-sensitive) and UMSCC10b/15s (Cisplatin-resistant) cell lines derived from human head and neck squamous cell cancer were lines were obtained from Dr. Stephen B. Howell of the University of California, Dan Diego. Cells were cultured in 1640 RPMI with 10% fetal bovine serum, 100 units/ml penicillin and 100 µg/ml of streptomycin. Cells were seeded into 24-well plates with approximately 20,000 cells/500 µl of media in each well plate. Cells were exposed to dach-2 with variable concentrations ranging from 1.12 µM to maximum of 72 µM. Stock solutions of dach-2 complex were prepared and aliquots of these solutions were added to make those effective concentrations. Cells were then allowed to grow for 72 hours. Twelve different concentrations were used in this study. Each concentration had one control for a total of 12 controls.

The IC50 for UMSCC10b (Cisplatin-sensitive) can be estimated to be below 1.0 µM. In comparison, the IC50 value for cisplatin is 17 µM in the same line (See Zheng et al., Clinical Cancer Research, 1997, 3, 1157-1165). The IC50 for UMSCC10b/15s (Cisplatin-resistant) was determined to be 5 µM. FIG. 9 shows the cell survival curve for the cisplatin-sensitive and cisplatin-resistant cell lines.

Example 11

Preliminary gene expression experiments involving complexes of the present invention as compared to cisplatin (data not shown) were carried out with an apoptotic array containing 84 genes that includes the BCL2 superfamily, both pro- and anti-apoptotic, caspases, the BIR-family, TNF receptor activator factors, p53 and its congeners, and fas associated members by real-time PCR. A closer look at the two sets of gene expressions clearly indicates a number of differences in the expression patterns. For example, fas and members of the fas superfamily genes were overexpressed in cells treated with dach-2 while the cisplatin influenced marginal changes in the expression of these genes. Specifically, fas was overexpressed by 6-fold compared to the control, and TNFRS genes such as TNFRSF-10B was overexpressed by 2-3 folds over controls. These latter receptor factors belong to the fas superfamily. It is interesting to note that proapoptotic BCL2 members such as BAK1 and BAX were overexpressed about 2-3 folds by dach-2 while cisplatin did not make significant changes in their expression.

Example 12

Cellular Accumulation of Platinum and Estimation of DNA-Bound Platinum

Platinum content was quantitatively estimated on a Graphite Furnace Atomic Absorption Spectrometer (Perkin Elmer AA-600) from calibration curves established by using cisplatin or pyrodach-2 in water. Cells ($5 \times 10^6$) were seeded in T75 $cm^2$ flasks. After 24 h, these cells were then treated with the different concentrations (0, 10, 20, 30 and 50 µM) of cisplatin and pyrodach-2. After 1 hr exposure with the platinum complexes, the drug-containing medium was removed and the cells were washed with ice-cold phosphate-buffered saline (PBS). The cells were then trypsinized and centrifuged into a pellet. Cell pellets were digested in concentrated $HNO_3$ and $H_2O_2$ prior to analysis, according to the method of McGahan. Data reported in Table 4 were collected from three independent experiments each was carried out in duplicate. For the cisplatin accumulation, data were obtained from triplicate runs from a single sample at a given concentration.

For DNA-Pt measurements, $1.0 \times 10^7$ cells were seeded in T75 $cm^2$ flasks. After 24 hr, the platinum complexes were added at the different concentrations 0, 10, 20, 30 and 50 μM. Cells were treated with the platinum complexes for 24 hours. Following treatment, the medium was removed and cells were washed with ice-cold PBS. The cells were trypsinized and centrifuged into a pellet. DNA was extracted using a Wizard® SV DNA purification kit (Promega). The DNA was quantitatively estimated from the absorption at 260 nm using a Nanoprop UV-Vis instrument.

Example 13

Platinum-DNA Binding by NMR

Proton NMR spectroscopic experiments were conducted on a Bruker 500 MHz NMR instrument in 99% (atom) $D_2O$ with a water suppression pulse sequence. Samples contained cisplatin (2.0 mM) or pyrodach-2 (2.0 mM) and nucleotides (5'-dGMP, 5'-dAMP, dGpG (5.0 mM)), and, single- and double stranded DNA (calf thymus, 5.0 mM) at pH 7.0 maintained by phosphate and carbonate buffers (10-20 mM). Reactions of cisplatin (0.25 mM) and pyrodach-2 (0.25 mM) with a synthetic 25-mer: 5'-ATGATTTAGGTGACACTAT-AGCAGT-3' (SEQ ID NO: 1) (0.25 mM) were also performed under identical conditions. Reactions were carried out up to 7 days, and $^1H$ and $^{31}P$ NMR spectra were recorded at regular time intervals. Usually, a pulse width of 5 μs with a 1.0 s repetition delay was used for the measurements. Typically, a sweepwidth of 10,000 Hz and 32 K data points were selected to collect the Free Induction Decays. A line broadening factor of 1 Hz was for applied Fourier transformation. The chemical shifts, with reference to H—O-D peak, are at 4.67 ppm.

amines wherein each $R^3$ is selected from substituted or unsubstituted aliphatic or aromatic diamines;

wherein $R^1$ and $R^2$ are not both $NH_3$; and wherein each S is independently selected from hydroxide, acetic acid, butyric acid, and alpha-hydroxy acids; or pharmaceutically acceptable salts thereof.

2. The composition of claim 1, wherein $R^1$ and $R^2$ are each independently selected from $NH_3$, methyl amine, ethyl amine, propyl amine, isopropyl amine, butyl amine, cyclohexane amine, aniline, pyridine, and substituted pyridine.

3. The composition of claim 1, wherein $R^3$ is selected from ethylenediamine and cyclohexanediamine.

4. A composition for treating cancer, comprising:
one or more isolated monomeric platinum complexes of the formula III as set forth in FIG. 1;
wherein $R^3$ is selected from ethylenediamine and cyclohexanediamine;
wherein at least one of the one or more isolated monomeric platinum complexes is (Trans-1,2-cyclohexanediamine)(dihydrogen pyrophosphato)platinum (II).

5. A composition for treating cancer, comprising:
one or more isolated monomeric platinum complexes of the formula II as set forth in FIG. 1;
wherein each $R^1$ and each $R^2$ is independently selected from $NH_3$, methyl amine, ethyl amine, propyl amine, isopropyl amine, butyl amine, cyclohexane amine, aniline, pyridine, and substituted pyridines; and
wherein each S is independently selected from hydroxide, acetic acid, butyric acid, and alpha-hydroxy acids; or
pharmaceutically acceptable salts thereof.

6. The composition of claim 1, wherein at least one of the one or more isolated monomeric platinum complexes is Trans-1,2-cyclohexanediamine)-trans-dihyroxo(dihydrogen pyrophosphato)platinum(IV).

7. A composition for treating cancer, comprising:
one or more isolated monomeric platinum complexes selected from:

What is claimed is:

1. A composition for treating cancer, comprising:
one or more isolated monomeric platinum complexes of the formulas I, II, and IV as set forth in FIG. 1;
wherein each $R^1$ and each $R^2$ is independently selected from $NH_3$, substituted or unsubstituted aliphatic amines, and substituted or unsubstituted aromatic (i) cis-diammine-trans-dihydroxo(dihydrogen pyrophosphato)platinum(IV);
(ii) (Trans-1,2-cyclohexanediamine)(dihydrogen pyrophosphato)platinum(II);
(iii) (Trans-1,2-cyclohexanediamine)-trans-dihydroxo (dihydrogen pyrophosphato)platinum(IV); and
(iv) pharmaceutically acceptable salts thereof;

wherein each isolated monomeric platinum complex or salt thereof is stable in aqueous solution at a pH of from about 6 to about 8.

8. A method of preparing an isolated monomeric platinum (IV) complex, comprising:
(i) maintaining an aqueous reaction mixture comprising excess pyrophosphate and a platinum complex of the formula VI as set forth in FIG. 15:
wherein $R^3$ is trans-1,2-cyclohexanediamine, and wherein each X is independently selected from halogens;
at a temperature of about 30° C. to about 60° C. for a period of about 12 hours to about 18 hours at a pH of from about 7 to about 9;
(ii) adding to the reaction mixture hydrogen peroxide, and optionally a reagent selected from the group of acetate salts, butyrate salts, and salts of alpha-hydroxy acids, and combinations thereof;
(iii) subsequently concentrating the aqueous reaction mixture such that precipitates of pyrophosphate do not form;
(iv) rapidly lowering the pH of the aqueous reaction mixture to a pH of less than 2 by addition of nitric acid;
wherein the isolated monomeric platinum complex prepared is (Trans-1,2-cyclohexanediamine)-trans-dihydroxo(dihydrogen pyrophosphato)platinum(IV); and
wherein the isolated monomeric platinum complex is stable in aqueous solution at a pH of from about 6 to about 9.

9. The composition of claim 5, wherein at least one of the one or more isolated monomeric platinum complexes is cis-diammine-trans-dihydroxo(dihydrogen pyrophosphato)platinum(IV).

10. A compound for treating cancer, comprising;
an isolated monomeric pyrophosphate-platinum complex comprising a platinum center selected from Pt(II) and Pt(IV) and having a formula selected from I, II, III, and IV, as set forth in FIG. 1;
wherein each $R^1$ and $R^2$ is independently selected from $NH_3$, methyl amine, ethyl amine, propyl amine, isopropyl amine, butyl amine, cyclohexane amine, aniline, pyridine, and substituted pyridine;
wherein $R^3$ is selected from substituted or unsubstituted aliphatic or aromatic diamines; and
wherein each S is independently selected from hydroxide, acetic acid, butyric acid, and alpha-hydroxy acids;
wherein the isolated monomeric pyrophosphate-platinum complex effects expression of one or more proapoptotic genes selected from Fas, Bak, and Bax and does not bind DNA; and
wherein the compound does not comprise diammine(dihydrogen pyrophosphato)platinum(II).

11. A compound according to claim 10 that is cis-diammine-trans-dihydroxo(dihydrogen pyrophosphato)platinum (IV).

12. A method of increasing expression of one or more of Fas, Bak, and Bax, comprising:
administering to a subject one or more compounds that do not bind DNA, each compound comprising a pyrophosphate complexed with a platinum center selected from Pt(II) and Pt(IV);
wherein the compound effects expression of one or more of Fas, Bak, and Bax; and
wherein the compound is not diammine(dihydrogen pyrophosphato)platinum (II).

13. A method according to claim 12, wherein the one or more compounds administered are selected from isolated monomeric complexes of:
(i) cis-diammine-trans-dihydroxo(dihydrogen pyrophosphato)platinum(IV);
(ii) 1,2-Ethanediamine(dihydrogen pyrophosphato)platinum (II);
(iii) 1,2-Ethanediamine-trans-dihydroxo(dihydrogen pyrophosphato)platinum(IV);
(iv) (Trans-1,2-cyclohexanediamine)(dihydrogen pyrophosphato)platinum(II); and
(v) (Trans-1,2-cyclohexanediamine)-trans-dihyroxo(dihydrogen pyrophosphato)platinum(IV).

14. A method according to claim 13, wherein the subject has a cancer resistant to one or more of cisplatin, carboplatin, and oxaliplatin.

15. A method according to claim 14, wherein the cancer is selected from testicular, small cell lung, ovarian, and head and neck cancers.

16. A method of increasing expression of one or more of Fas, Bak, and Bax in target cells, comprising:
administering to a subject at least one platinum-containing compound selected from:
(a) an isolated monomeric platinum complex of the formula II as set forth in FIG. 1;
wherein $R^1$ and $R^2$ are each independently selected from $NH_3$, methyl amine, ethyl amine, propyl amine, isopropyl amine, butyl amine, cyclohexane amine, aniline, pyridine, and substituted pyridines; and
wherein each S is independently selected from hydroxide, acetic acid, butyric acid, and alpha-hydroxy acids; or
pharmaceutically acceptable salts thereof;
(b) an isolated monomeric platinum complex of the formulas I, II, and IV as set forth in FIG. 1;
wherein each $R^1$ and $R^2$ is independently selected from $NH_3$, substituted or unsubstituted aliphatic amines, and substituted or unsubstituted aromatic amines;
wherein each $R^3$ is selected from substituted or unsubstituted aliphatic or aromatic diamines;
wherein $R^1$ and $R^2$ are not both $NH_3$; and
wherein each S is independently selected from hydroxide, acetic acid, butyric acid, and alpha-hydroxy acids; or
pharmaceutically acceptable salts thereof; and
(c) an isolated monomeric platinum complex of the formula III as set forth in FIG. 1;
wherein $R^3$ is selected from substituted or unsubstituted aliphatic or aromatic amines; or
pharmaceutically acceptable salts thereof.

17. A method according to claim 16, wherein the subject has a cancer resistant to one or more of cisplatin, carboplatin, and oxaliplatin.

18. A method of treating cancer, comprising:
administering to a subject a therapeutically effective amount of a composition comprising (i) at least one pharmaceutically acceptable carrier, diluent, adjuvant, or vehicle; and (ii) one or more platinum-containing compounds selected from:
(a) an isolated monomeric platinum complex of the formula II as set forth in FIG. 1;
wherein each $R^1$ and $R^2$ is independently selected from $NH_3$, methyl amine, ethyl amine, propyl amine, isopropyl amine, butyl amine, cyclohexane amine, aniline, pyridine, and substituted pyridines; and wherein each S is independently selected from hydroxide, acetic acid, butyric acid, and alpha-hydroxy acids; or pharmaceutically acceptable salts thereof;

(b) an isolated monomeric platinum complex of the formulas I, II, and IV as set forth in FIG. 1;

wherein each $R^1$ and $R^2$ is independently selected from $NH_3$, substituted or unsubstituted aliphatic amines, and substituted or unsubstituted aromatic amines;

wherein each $R^3$ is selected from substituted or unsubstituted aliphatic or aromatic diamines;

wherein $R^1$ and $R^2$ are not both $NH_3$; and wherein each S is independently selected from hydroxide, acetic acid, butyric acid, and alpha-hydroxy acids; or pharmaceutically acceptable salts thereof; and (c) an isolated monomeric platinum complex of the formula III as set forth in FIG. 1;

wherein $R^3$ is selected from substituted or unsubstituted aliphatic or aromatic amines; or pharmaceutically acceptable salts thereof.

19. The method of claim 18, wherein the subject has a cancer resistant to one or more of cisplatin, carboplatin, and oxaliplatin.

20. The method of claim 19, wherein the cancer is ovarian.

21. A method of treating cancers that are resistant to cisplatin, carboplatin, oxaliplatin, or combinations thereof, comprising:

administering to a subject having a cancer selected from testicular, small cell lung, and head and neck cancer resistant to one or more of cisplatin, carboplatin, and oxaliplatin, a therapeutically effective amount of a composition comprising (i) at least one pharmaceutically acceptable carrier, diluent, adjuvant, or vehicle; and (ii) one or more platinum-containing compounds selected from:

(a) isolated monomeric complex of diammine(dihydrogen pyrophosphato)platinum(II); or pharmaceutically acceptable salt thereof;

(b) an isolated monomeric complex of cis-diamminetrans-dihydroxo(dihydrogen pyrophosphato) platinum (IV); or pharmaceutically acceptable salt thereof;

(c) an isolated monomeric platinum complex of the formulas I, II, and IV as set forth in FIG. 1;

wherein each $R^1$ and $R^2$ is independently selected from $NH_3$, substituted or unsubstituted aliphatic amines, and substituted or unsubstituted aromatic amines;

wherein each $R^3$ is selected from substituted or unsubstituted aliphatic or aromatic diamines;

wherein $R^1$ and $R^2$ are not both $NH_3$; and wherein each S is independently selected from hydroxide, acetic acid, butyric acid, and alpha-hydroxy acids; or pharmaceutically acceptable salts thereof; and (d) an isolated monomeric platinum complex of the formula III as set forth in FIG. 1;

wherein $R^3$ is selected from substituted or unsubstituted aliphatic or aromatic amines; or pharmaceutically acceptable salts thereof.

22. A composition for treating cancer, comprising:

one or more isolated monomeric platinum complexes of the formula I as set forth in FIG. 1;

wherein each $R^1$ and $R^2$ is independently selected from $NH_3$, methyl amine, ethyl amine, propyl amine, isopropyl amine, butyl amine, cyclohexane amine, aniline, pyridine, and substituted pyridines;

wherein $R^1$ and $R^2$ are not both $NH_3$; and wherein each S is independently selected from hydroxide, acetic acid, butyric acid, and alpha-hydroxy acids; or pharmaceutically acceptable salts thereof.

23. A composition for treating cancer, comprising:

one or more isolated monomeric platinum complexes of the formula IV as set forth in FIG. 1;

wherein $R^3$ is selected from substituted or unsubstituted aliphatic or aromatic diamines; and wherein each S is independently selected from hydroxide, acetic acid, butyric acid, and alpha-hydroxy acids; or pharmaceutically acceptable salts thereof.

24. A composition of claim 23, wherein $R^3$ is selected from ethylenediamine and cyclohexanediamine.

25. A composition for treating cancers that are resistant to cisplatin, carboplatin, oxaliplatin, or combinations thereof, comprising:

isolated monomeric platinum complexes of (Trans-1,2-cyclohexanediamine)(dihydrogen pyrophosphato)platinum(II); or pharmaceutically acceptable salt thereof.

26. A method of treating cancers that are resistant to cisplatin, carboplating, oxaliplatin, or combinations thereof, comprising:

administering to a subject having a cancer resistant to one or more of cisplatin, carboplatin, and oxaliplatin, a therapeutically effective amount of a composition of claim 25.

27. A method of claim 26, wherein the cancer is selected from testicular, small cell lung, and head and neck cancers.

28. A method claim 26, wherein the cancer is selected from ovarian.

29. A composition for treating cancers that are resistant to cisplatin, carboplatin, oxaliplatin, or combinations thereof, comprising:

isolated monomeric platinum complexes of (Trans-1,2-cyclohexanediamine)-trans-dihydroxo(dihydrogen pyrophosphato)platinum(IV); or pharmaceutically acceptable salts thereof.

30. A method of treating cancers that are resistant to cisplatin, carboplating, oxaliplatin, or combinations thereof, comprising:

administering to a subject having a cancer resistant to one or more of cisplatin, carboplatin, and oxaliplatin, a therapeutically effective amount of a composition of claim 29.

31. A method of claim 30, wherein the cancer is selected from testicular, small cell lung, and head and neck cancers.

32. A method of claim 30, wherein the cancer is selected from ovarian.

* * * * *